United States Patent
Moore et al.

(10) Patent No.: US 12,409,012 B2
(45) Date of Patent: Sep. 9, 2025

(54) DENTAL DEVICE

(71) Applicants: Paul Moore, Galway (IE); Hazel Hendy, Galway (IE)

(72) Inventors: Paul Moore, Galway (IE); Hazel Hendy, Galway (IE)

( * ) Notice: Subject to any disclaimer, the term of this patent is extended or adjusted under 35 U.S.C. 154(b) by 506 days.

(21) Appl. No.: 17/433,510

(22) PCT Filed: Feb. 25, 2020

(86) PCT No.: PCT/EP2020/054947
§ 371 (c)(1),
(2) Date: Aug. 24, 2021

(87) PCT Pub. No.: WO2020/173964
PCT Pub. Date: Sep. 3, 2020

(65) Prior Publication Data
US 2022/0142738 A1    May 12, 2022

(30) Foreign Application Priority Data
Feb. 25, 2019  (GB) .................................... 1902533

(51) Int. Cl.
*A61C 5/90*    (2017.01)
*A61C 5/82*    (2017.01)

(52) U.S. Cl.
CPC . *A61C 5/90* (2017.02); *A61C 5/82* (2017.02)

(58) Field of Classification Search
CPC .................................. A61C 5/90; A61C 5/82
See application file for complete search history.

(56) References Cited

U.S. PATENT DOCUMENTS

| | | | |
|---|---|---|---|
| 557,664 A * | 4/1896 | Gilbert | |
| 3,916,880 A | 11/1975 | Schroer | |
| 4,200,089 A * | 4/1980 | Inoue | A61B 1/24 600/206 |
| 4,889,491 A * | 12/1989 | Krygier | A61C 5/90 433/136 |
| 5,865,170 A * | 2/1999 | Moles | B63C 11/186 128/206.29 |
| 6,213,772 B1 * | 4/2001 | Costello | A61C 17/08 433/140 |
| 6,514,176 B1 * | 2/2003 | Norton | A63B 23/032 128/857 |

(Continued)

FOREIGN PATENT DOCUMENTS

| | | |
|---|---|---|
| EP | 2085048 A1 | 8/2009 |
| JP | S50-19908 Y1 | 6/1970 |

(Continued)

OTHER PUBLICATIONS

Japanese Decision of Refusal dated Jun. 4, 2024 for Japanese Patent Application No. 2021-550099.

*Primary Examiner* — Ralph A Lewis
(74) *Attorney, Agent, or Firm* — Fishman Stewart PLLC

(57) ABSTRACT

Aspects of the present invention relate to a dental retractor for controlling the position of soft tissue within a mouth, the dental retractor comprising: a lip retractor for controlling the position of a lip; and a cheek retractor comprising a pair of arms for controlling the position of a cheek; and wherein the dental retractor comprises a tongue retractor removably coupled to the dental retractor for controlling the position of a tongue.

11 Claims, 18 Drawing Sheets

(56) References Cited

U.S. PATENT DOCUMENTS

| | | | |
|---|---|---|---|
| 6,679,257 B1* | 1/2004 | Robertson | A61M 16/0493 |
| | | | 128/204.18 |
| 6,966,319 B2* | 11/2005 | Fitton | A62B 9/06 |
| | | | 128/859 |
| D634,841 S* | 3/2011 | Tao | D24/152 |
| 8,172,570 B2 | 5/2012 | Baughman | |
| D806,872 S* | 1/2018 | Jablow | D24/176 |
| 9,901,332 B2 | 2/2018 | Jessop | |
| 2006/0019216 A1* | 1/2006 | Priluck | A61C 5/90 |
| | | | 433/140 |
| 2006/0234187 A1* | 10/2006 | Kilcher | A61C 5/90 |
| | | | 433/140 |
| 2009/0081611 A1 | 3/2009 | Hines | |
| 2010/0119989 A1* | 5/2010 | Raybuck | A61C 5/90 |
| | | | 264/16 |
| 2013/0104913 A1* | 5/2013 | Evans | A63B 71/085 |
| | | | 128/861 |
| 2013/0133648 A1* | 5/2013 | Beach | B63C 11/186 |
| | | | 128/207.14 |
| 2016/0022381 A1* | 1/2016 | Jessop | A61B 17/02 |
| | | | 433/140 |
| 2016/0361192 A1* | 12/2016 | Gerschman | A61F 5/566 |
| 2017/0000586 A1* | 1/2017 | Lesser | A61C 5/90 |
| 2021/0186657 A1* | 6/2021 | Abdalla Sabeal Mohamed Al Bloushi | A61C 5/82 |
| 2022/0370053 A1* | 11/2022 | Tollini | A61B 90/16 |

FOREIGN PATENT DOCUMENTS

| | | |
|---|---|---|
| JP | H11-178792 A | 7/1999 |
| JP | 2005511232 A | 4/2005 |
| JP | 2006514861 A | 5/2006 |
| JP | 2009532126 A | 9/2009 |
| JP | 2016517326 A | 6/2016 |
| WO | 20140143911 A1 | 9/2014 |

* cited by examiner

DENTAL DEVICE

TECHNICAL FIELD

The present disclosure relates to a dental device, and in particular but not exclusively, to a dental retractor for controlling the position of soft tissue within a patient's mouth. Aspects of the invention relate to a dental retractor, to a dental contraster, to a tongue retractor and to a sheet.

BACKGROUND

During a dental procedure dentists require unobstructed access to a patient's mouth. Typically this is achieved by the patient holding their mouth open for a sustained period of time during the procedure in order to provide access to their teeth. During a dental procedure the dentist may be assisted by a dental assistant who can hold, for example, the patient's cheeks or lips out of the way of the dentist to avoid any unwanted obstructions during the dental procedure.

It is known to use various tools to aid the dentist or their assistant during a procedure. For example, a dentist may use a retractor device to control the position of soft tissue, such as the tongue, lips or cheeks, during a dental procedure. This is beneficial as the position of the soft tissue may be controlled to provide unobstructed access to a patient's mouth during a dental procedure, however, the retractors of the prior art are difficult to accurately position and often require a dental assistant to hold them in place during a procedure.

This problem is often compounded during dental photography procedures. During a photography procedure it is desirable to photograph a patient's teeth against a black background such that the white of the teeth is contrasted against the dark background. Typically, this is achieved by positioning a further dental tool in the patient's mouth known as a dental contraster. A dental contraster is typically a sheet of black metal that is inserted into a patient's mouth behind the top or bottom teeth to provide a dark background against which the teeth may be photographed.

However, positioning the dental contraster within the patient's mouth whilst simultaneously photographing the patient's teeth is a complex process due to the number of components required to be accurately positioned and held steady. For example, a dentist may be required to fit one or more retractor tools to control the position of the soft tissue within a patient's mouth such that the teeth are visible and then to further position a contraster within a patient's mouth such that the teeth may be photographed against a black background.

This complex procedure presents a number of challenges that the dentist must overcome. Firstly, positioning multiple retractors within a patient's mouth is time consuming and uncomfortable for a patient. Often the retractors have to be held in place by a dental assistant, which further inhibits access to a patient's mouth. Furthermore, locating a dental contraster within a patient's mouth adds an additional level of discomfort for the patient and in some cases may invoke a gag reflex. The dentist must position the retractor with one hand and photograph the patient's mouth using the other hand, which represents significant ergonomic challenges and can result in a low quality image.

Furthermore, this process is further complicated if the dentist wants to simultaneously photograph the lower and upper teeth as separate dental contrasters are required to be inserted for the lower and upper dental arches. It is not only difficult to position separate dental contrasters within a patient's mouth but it is also uncomfortable for a patient and only the upper or the lower teeth can be backed by the contraster at any one time.

It is an aim of the present invention to address one or more of the disadvantages associated with the prior art.

SUMMARY OF THE INVENTION

According to an aspect of the present invention there is provided a dental retractor for controlling the position of soft tissue within a patient's mouth, the dental retractor comprising a lip retractor for controlling the position of the patient's lips and a cheek retractor comprising a pair of arms connected to the lip retractor for controlling the position of the patient's cheeks. The pair of arms may be arched to follow the path of the dental arch. Furthermore, the pair of arms may be configured to control the position of opposing cheeks of the patient. The arms may be an integral part of the lip retractor or may be integrally formed with the lip retractor.

The dental retractor may comprise a tongue retractor. The tongue retractor may be removably coupled to the dental retractor or the tongue retractor may be attached to the cheek retractor permanently.

According to an aspect of the present invention there is provided a dental retractor for controlling the position of soft tissue within a mouth, the dental retractor comprising: a lip retractor for controlling the position of a lip; and a cheek retractor comprising a pair of arms for controlling the position of a cheek; and wherein the dental retractor comprises a tongue retractor removably coupled to the dental retractor for controlling the position of a tongue. The lip retractor may be circumferentially continuous around, and peripheral relative to, an opening. The pair of arms may be connected to, and extend distally from, the lip retractor.

Advantageously, the dental retractor combines the features of a lip retractor, cheek retractor and tongue retractor into a single device that may be easily located within a patient's mouth. The tongue retractor is beneficially removably coupled to the dental retractor such that it may be removed if it is not required during a dental procedure. Furthermore, the dental device may control the position of the soft tissue within a patient's mouth such that unobstructed access is provided to the patient's teeth for the dentist during a dental procedure. The arms may be an integral part of the lip retractor or they may be integrally attached to the lip retractor.

In an embodiment the pair of arms may be arched in plan view. In another embodiment the pair of arms may form an arch representative of a dental arch. The opening may extend through a portion of the arms. This is advantageous as arching the arms of the cheek retractor improves the comfort of the cheek retractor for the patient. Furthermore, the cheek retractor may extend along the length of the lower and upper dental arches thereby retracting the cheek along the entire dental arch. The arched arms may be located outward of the dental arch to push the patient's cheeks outward and away from their teeth to provide space for a dentist to perform a procedure on the patient.

Beneficially, because the pair of arms may extend along the entire dental arch the arms also promote forward movement of a patient's lips. As such the pair of arms may also form part of the lip retractor. The arms may promote forward movement of the patient's lips to create a gap between the patient's lips and front teeth, thereby retracting the lips and providing space for a dentist to work on the patient's teeth.

In another embodiment the pair of arms may extend in a rearward or distal direction relative to the lip retractor. This is beneficial as the arms may extend distally relative to the lip retractor to follow the path of the patient's dental arch. As such the pair of arms may retract the cheeks along the entire length of the dental arch. Typically, the pair of arms are located on opposing sides of the dental retractor such that each arm retracts opposing cheeks. The arms may form a continuous arch extending distally along an arched path, in plan view. The arms of the cheek retractor may be joined to the lip retractor at the point the arch changes direction.

In one embodiment the pair of arms may taper as they extend in the distal direction. The taper may reduce the vertical height of the arms in the distal direction. Advantageously, the arms may taper to follow the angle between the lower and upper dental arches when the patient's mouth is open thereby improving the comfort of the dental retractor. Furthermore, the taper makes it easier for a patient to close their mouth as the arms are less likely to cause pain or discomfort when the patient closes their mouth.

The skilled reader will understand that the term distal relates to a rearward direction with respect to a patient's mouth and the term proximal relates to a forward direction with respect to a patient's mouth. The term plan view relates to a view looking at the dental retractor from above such that the plan view is substantially orthogonal to the aforementioned rearward and forward directions.

In an embodiment the arms may comprise a deformable flange. The deformable flange may extend along an upper and a lower edge of the pair of arms. The deformable flange may be configured to deform and mould to the soft internal tissue of a patient's mouth when the mouth is both open and closed. In another embodiment the length of the deformable flange may increase as the arms extend in the distal direction. For example, the vertical height of the flange may increase as the arms extend in the distal direction. This is beneficial as the arms may taper in the distal or rearward direction and as such the increasing flange length advantageously maintains contact with the lower and upper buccal sulcus thereby ensuring the cheek remains suitably retracted when the mouth is open and closed along the entire length of the dental arch.

In another embodiment the lip retractor may be a circumferential lip retractor. The lip retractor may define a central aperture or opening to provide access to the patient's mouth. This is advantageous as the circumferential lip retractor may retract a patient's lips around the entire ovoid of the front of the mouth. This improves the access path provided to the dentist by the lip retractor by ensuring the patient's lips are retracted around the entire mouth.

In one embodiment the circumferential lip retractor may comprise a radially extending flange for locating the dental retractor in the mouth. The radially extending flange may wrap around the patient's lips and act to centre the dental retractor within the patient's mouth. Furthermore, the flange may contact the outer surface of a patient's lips thus preventing the dental retractor inadvertently being located too deeply within a patient's mouth which may cause discomfort and invoke a gag reflex from the patient.

In an embodiment the lip retractor may define an aperture for accessing the mouth of the patient. This is advantageous as the lip retractor may control the position of a patient's lips to retract and distance them from a patient's teeth. The central aperture defined by the lip retractor may then provide access to the patient's mouth through the channel created by retracting the patient's lips.

In another embodiment the tongue retractor may be U-shaped when viewed in a plan view. The U-shaped profile of the tongue retractor may be shaped to match the arch of the lingual surfaces of the tongue. Furthermore, the U-shaped profile may wrap around the patient's tongue such that the tongue is retracted securely and the patient is unable to move their tongue into the working space. This protects the soft tissues from the procedure being carried out. Furthermore, the U-shaped profile makes the tongue retractor easier to position as the U-shape may capture the tongue and act as a guide to guide the tongue into the tongue retractor.

In an embodiment the tongue retractor may comprise a strap for attaching the tongue retractor to the dental retractor. This is beneficial as the strap may easily be secured to the dental retractor such that the tongue retractor is similarly secured to the dental retractor. Furthermore, the strap may be easily removed if the dentist wishes to perform a procedure where the tongue retractor is not required.

In one embodiment the pair of arms may comprise a channel for securing the strap to the dental retractor. In another embodiment the channel may comprise an overhanging lip along the length of the channel, to provide a snap-fit retention of the strap. In a further embodiment the strap may comprise a tab for gripping the strap. The strap may be moveable in the channel with respect to the arms to adjust the position of the tongue retractor relative to the dental retractor. Advantageously, the strap may be located by a snap-fit within the channel to prevent the strap accidentally being dislodged from the channel. Furthermore, the strap may also be slid through the channel, relative to the dental retractor, to adjust the position of the tongue retractor such that the patient is comfortable when their tongue is retracted.

In another embodiment the tongue retractor may comprise a notch for receiving the lingual frenum. This is beneficial as it enables the tongue to be retracted further by accommodating the lingual frenum and also improves the comfort of the tongue retractor for the patient.

In an embodiment the tongue retractor may comprise a recess for partially receiving the tip of the tongue. This is beneficial as the recess may help to retain the tongue in the retracted position when the tongue retractor retracts the patient's tongue.

In another embodiment the tongue retractor may be deformable to mould to the mouth when the mouth is open or closed. The tongue retractor may comprise lower and upper flanges for contacting the floor and ceiling of the mouth respectively. The lower and upper flanges may be thinner than a central portion of the tongue retractor. The thinner flanges may be configured to maintain contact with the ceiling and roof of the patient's mouth when the mouth is closed or open.

In one embodiment the lip retractor may comprise a visual marker to indicate a centreline. This is beneficial as the centreline may be used by the dentist when performing the dental procedure as an alignment aid. Furthermore, the visual marker may also be indicative of the size of the dental retractor, for example, size 1, size 2 or size 3. The visual marker may include a number of raised or embossed buttons or features wherein the number of raised features in the midline on the front outer surface of the lip retractor is indicative of the size of the retractor.

In an embodiment the dental retractor and/or the tongue retractor are made from medical grade silicone. This is advantageous as medical grade silicone is relatively soft and thus comfortable for the patient compared to a metallic material or a hard plastics material. Furthermore, medical grade silicone is autoclavable and thus easily sterilised.

Medical grade silicone is also resiliently deformable such that the dental retractor may deform slightly to mould to the shape of the patient's mouth but then also return to the original shape after use.

In an embodiment the dental retractor and/or the tongue retractor may be a dark colour such as black. This is beneficial as the dental retractor may be used as a dental contraster for dental photography procedures. The dental retractor as described above may cover the inner surface of a patient's lips and cheeks and as such the dental retractor may provide a black background against which an image of the teeth may be taken. Furthermore, the tongue retractor may also be black. The tongue retractor may contact the ceiling and floor of a patient's mouth and as such the majority of the soft tissue within a patient's mouth may be obscured by the dental retractor. This is beneficial as the teeth of the patient may then be photographed against the dark background provided by the dental retractor and tongue retractor both when the patient's mouth is open and closed. Furthermore, the lower and upper dental arches may be photographed simultaneously.

According to another aspect of the present invention there is provided a tongue retractor for use with the dental retractor according to any one of the aforementioned aspects or embodiments.

According to a yet further aspect of the present invention there is provided a dental retractor for controlling the position of soft tissue within a patient's mouth, the dental retractor comprising: a lip retractor for controlling the position of the patient's lips; a cheek retractor comprising a pair of arms for controlling the position of the patient's cheeks; and a sheet secured to the lip retractor and extending over at least a portion of a front surface of the lip retractor, for example, over an opening on the lip retractor. The lip retractor may be circumferentially continuous around, and peripheral relative to, an opening and the sheet may be secured to the lip retractor and extending over the opening. The sheet may engage or wrap around a radially extending flange of the lip retractor.

Beneficially, the sheet may be used as a rubber dam during a dental procedure in which the dental retractor controls the position of the soft tissue within a patient's mouth. The dental retractor improves the comfort of the procedure for the patient whilst also making the procedure easier to perform for the dentist. The sheet may be easily attached to and removed from the front surface of the lip retractor.

In an embodiment the lip retractor may comprise a radially extending flange. In another embodiment the sheet may extend around at least a portion of the flange thereby securing the sheet to the lip retractor. This is beneficial as the sheet may be easily wrapped around the lip retractor thereby securing the sheet to the lip retractor, in use.

In a further embodiment the lip retractor may comprise a retention formation for securing the sheet to the lip retractor. The one or more formations may be positioned on a front surface of the lip retractor. In an embodiment the one or more retention formations may be positioned on a rear surface of the lip retractor. The one or more retention formations may comprise at least one of: a groove, a protrusion, a hook, a flange, for example a radially extending flange, and a ridge.

The sheet may comprise a cord extending around a peripheral edge of the sheet. The cord may be configured to secure the sheet to the lip retractor. For example, the sheet may wrap around a portion of the flange of the lip retractor and the cord may engage the rear surface of the lip retractor thereby securing the sheet to the lip retractor. The cord may be elastomeric and may be configured to engage the one or more retention features on the lip retractor so as to retain the sheet on the lip retractor. The elastomeric cord beneficially facilitates easy attachment and removal of the sheet.

In another embodiment the lip retractor may comprise a central aperture or opening and the sheet may be at least partially received within the central aperture. This is beneficial as the sheet may generally follow the profile of the patient's lower and upper dental arches. The sheet may comprise a dome portion and the dome portion may be configured to at least partially be received within the central aperture.

The sheet may comprise indicators to indicate the position of the patient's teeth relative to the sheet, in use. The indicators may be, for example, printed marks on the sheet or protrusions on the surface of the sheet corresponding to the position of the patient's teeth relative to the sheet.

The sheet may comprise one or more breathing holes located on the sheet. The breathing holes allow the patient to breathe through their mouth during the procedure and further allows a dentist to use a saliva ejector to remove saliva from the patient's mouth during a dental procedure. The breathing holes may be offset laterally from a central horizontal axis of the sheet. This is beneficial as it allows the dentist to position the holes proximal to either the lower or the upper arches depending on the position of the operative site in the dental procedure.

In another embodiment the sheet may comprise an aperture for receiving an endoscope during an endoscopy procedure. The aperture may comprise a reinforced rim so as to prevent the aperture tearing or ripping from contact with the endoscope.

A mouthpiece may be received within the aperture in the sheet. The mouthpiece may comprise a body portion and the body portion may further comprise channel for receiving an endoscope. The mouthpiece beneficially protects the endoscope from the patient's teeth. Furthermore, the mouthpiece may engage the aperture to locate and stabilise the endoscope during a procedure. The mouthpiece may comprise a flange extending around the body portion and the flange may be configured to engage the sheet so as to support the mouthpiece, in use.

In an embodiment the sheet may be made from an elastomeric material. The elastomeric sheet is advantageous as it may be stretched to facilitate easier attachment to the dental retractor. Furthermore, the elastomeric sheet may beneficially be stretched so as to engage one or more teeth of the patient when it is used as a rubber dam. The sheet may beneficially stretch and form a seal around a patient's tooth.

In another embodiment the dental retractor may comprise a tongue retractor for controlling the position of the patient's tongue. This is beneficial as the tongue retractor may inhibit the position of the patient's tongue during a dental procedure. This would prevent the patient's tongue from contacting the sheet during a procedure. In an embodiment the mouthpiece may be the tongue retractor. In another embodiment the tongue retractor may be removable coupled to the cheek retractor as outlined in any one of the aforementioned aspects or embodiments.

According to an aspect of the present invention there is provided a sheet for use with the dental retractor as outlined in any one of the aforementioned embodiments and aspects.

According to a yet further aspect of the present invention there is provided a dental retractor for controlling the position of soft tissue within a patient's mouth, the dental retractor comprising: a lip retractor for controlling the position of the patient's lips wherein the lip retractor is circumferentially continuous around, and peripheral relative to, an opening; and a cheek retractor comprising a pair of arms for controlling the position of the patient's cheeks; wherein the lip retractor comprises one or more retention formations on the periphery of the opening for removable attachment of a sheet over the opening.

In an embodiment the lip retractor may comprise a radially extending flange. The one or more formations may be positioned on a rear surface of the lip retractor. In another embodiment the one or more formations are positioned on a front surface of the lip retractor. The one or more retention formations may be at least one of: a groove, a protrusion a hook and a ridge.

According to another aspect of the present invention there is provided a sheet comprising retention formations for removable attachment of the sheet to the dental retractor as outlined in any one of the aforementioned embodiments and aspects.

In an embodiment the sheet may comprise a cord extending around a peripheral edge of the sheet. The cord may be elastomeric and may be configured to engage the one or more retention features on the lip retractor so as to retain the sheet on the lip retractor.

The sheet may comprise a domed portion. The domed portion may beneficially be received within a central aperture of the lip retractor such that the domed portion of the sheet generally follows the profile of the patient's mouth. The sheet may comprise indicators to indicate the position of the patient's teeth relative to the sheet, in use.

In another embodiment the sheet may comprise an aperture for receiving an endoscope. The aperture may comprise a reinforced rim. In a further embodiment the sheet may comprise one or more breathing holes. The one or more breathing holes may be offset laterally from a central horizontal axis of the sheet. In an embodiment the sheet may be made from an elastomeric material such as silicon, latex or nitrile.

According to a yet further aspect of the present invention there is provided a dental retractor as outlined in any one of the aforementioned aspects or embodiments comprising a sheet as outlined in any one of the aforementioned aspects or embodiments.

BRIEF DESCRIPTION OF THE DRAWINGS

One or more embodiments of the invention will now be described, by way of example only, with reference to the accompanying drawings, in which.

DETAILED DESCRIPTION

In general terms, embodiments of the invention relate to a dental retractor for controlling the position of soft tissue, such as the tongue, cheeks and lips, within the mouth of a dental patient during a dental procedure. The retractor comprises a circumferential lip retractor for promoting movement of a patient's lips away from their teeth such that the patient's lips do not obscure their teeth from view. The retractor further comprises a cheek retractor for moving the inner surface of a patient's cheek away from their lower and upper dental arches. The cheek retractor may comprise a pair of arcuate arms extending distally from the lip retractor along an arcuate path representative of the dental arch.

A tongue retractor may be removably coupled to the cheek retractor to control movement of a patient's tongue. The tongue retractor beneficially prevents the patient moving their tongue during a dental procedure as this may inhibit the dentist during the procedure. Furthermore, the removable tongue retractor enables the dental retractor to be used alone or in combination with the tongue retractor depending on the nature of the dental procedure.

Furthermore, the dental retractor may be made from matt black material, for example medical grade silicone, such that the dental retractor provides a matt black background against which the dentist may photograph a patient's teeth, without incurring reflections from flash photography. This is beneficial as the dental retractor can double as a dental contraster that may be easily positioned and worn by a patient during to allow a dentist to photograph the patient's teeth. Furthermore, the dental retractor can be used when the patient's jaws are open or closed thereby allowing the dentist to easily photograph the patient's teeth both when their mouth is open and when their mouth is closed.

Figure 1:
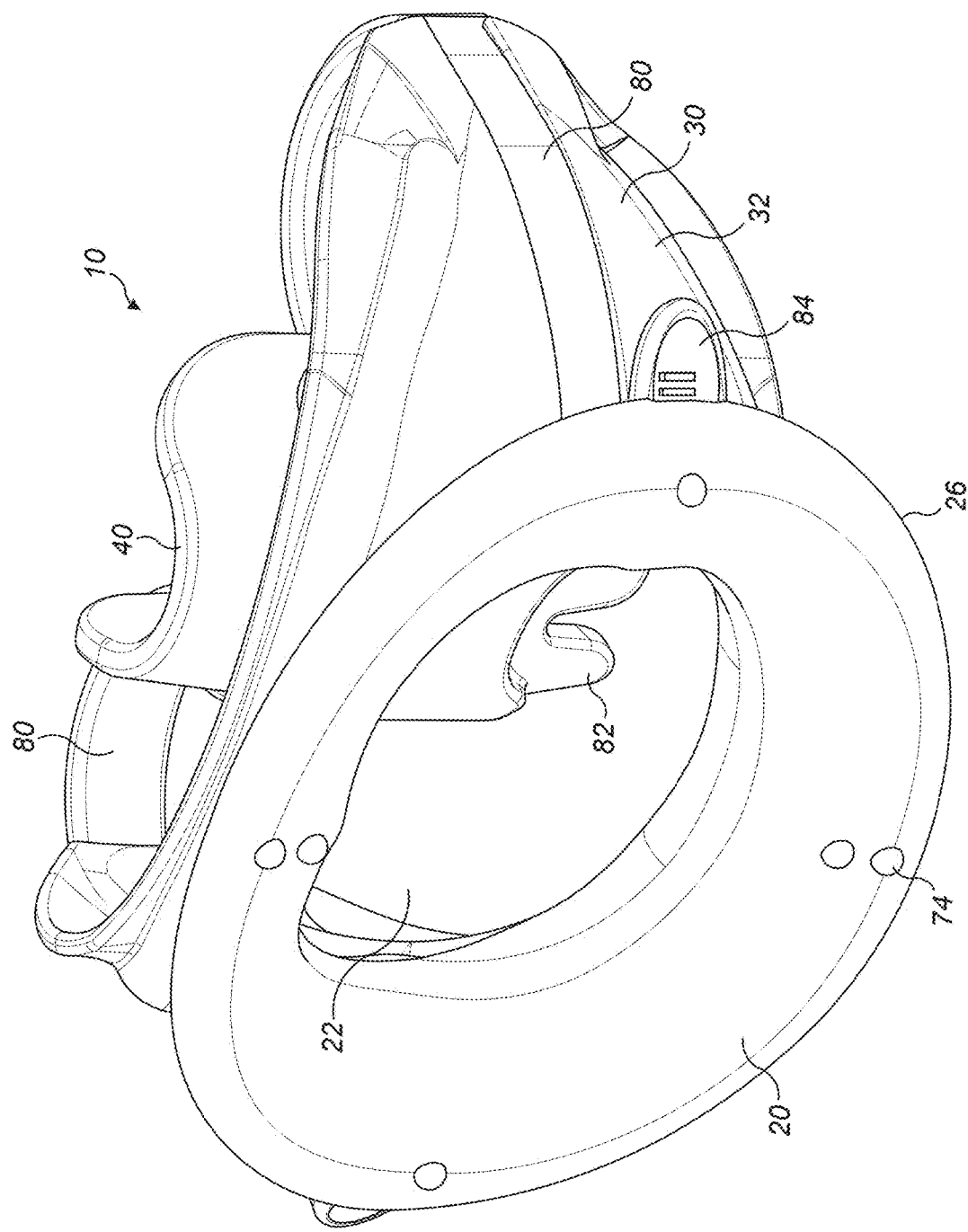
FIG. 1 is a front perspective view of a dental retractor according to embodiments of the invention.

To place embodiments of the invention in a suitable context, reference will firstly be made to FIG. 1 which shows a perspective view of the dental retractor 10. The retractor 10 comprises a lip retractor 20 for controlling the position of a patient's lips and a cheek retractor for controlling the position of a patient's cheeks. The retractor 10 also comprises a removable tongue retractor 40 attached to the retractor 10 for controlling the position of a patient's tongue when the retractor 10 is positioned within a patient's mouth.

Figure 2:
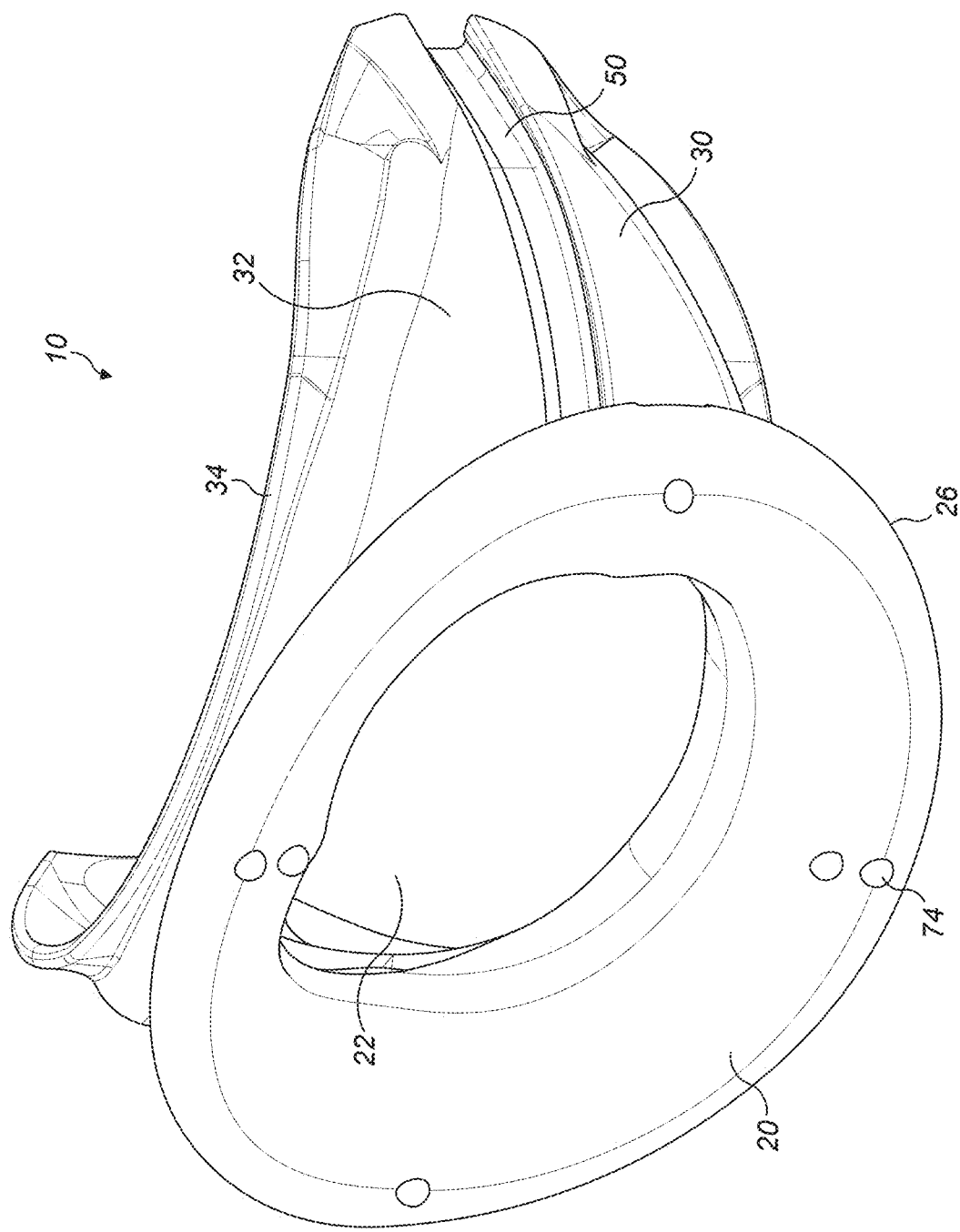
FIG. 2 is a front perspective view of the dental retractor of FIG. 1 with the tongue retractor removed.

Turning to FIG. 2, a perspective view of the retractor 10 with the tongue retractor 40 removed is shown. The lip retractor 20 is a circumferential lip retractor 20 for retaining a patient's lip away from the patient's teeth around the entire opening of the patient's mouth. The circumferential lip retractor 20 comprises an annulus with a central aperture 22. The lip retractor 20 distances the patient's lips from their front teeth and the central aperture 22 provides unobstructed access to a patient's mouth for the dentist when the retractor 10 is positioned within a patient's mouth.

Furthermore, the retractor 10 comprises a cheek retractor 30. The cheek retractor 30 comprises a pair of rearwardly or distally extending arms 32 connected to the lip retractor 20. The cheek retractor 30 is configured to control the position of the soft tissue of a patient's cheek such that when the retractor 10 is positioned within a patient's mouth the internal surface of the patient's cheeks contact the arms 32 and are pushed in an outward direction, away from the dental arch of the patient. This is beneficial as the cheek retractor 30 prevents the patient's cheeks contacting the dental arch and teeth of the patient which may inhibit the dentist during a dental procedure.

Figure 3:
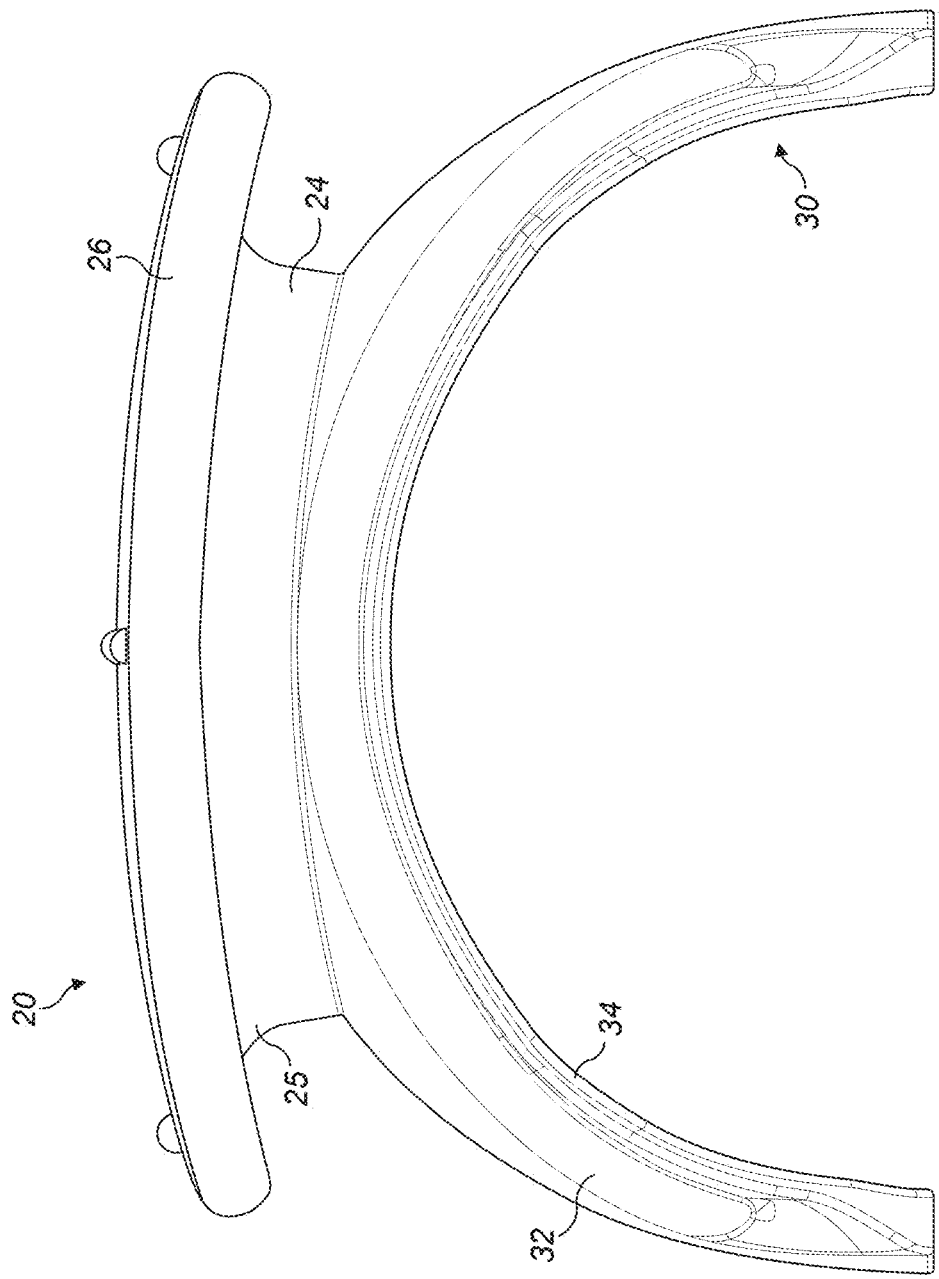
FIG. 3 is a plan view of the dental retractor of FIG. 2.
Figure 4:
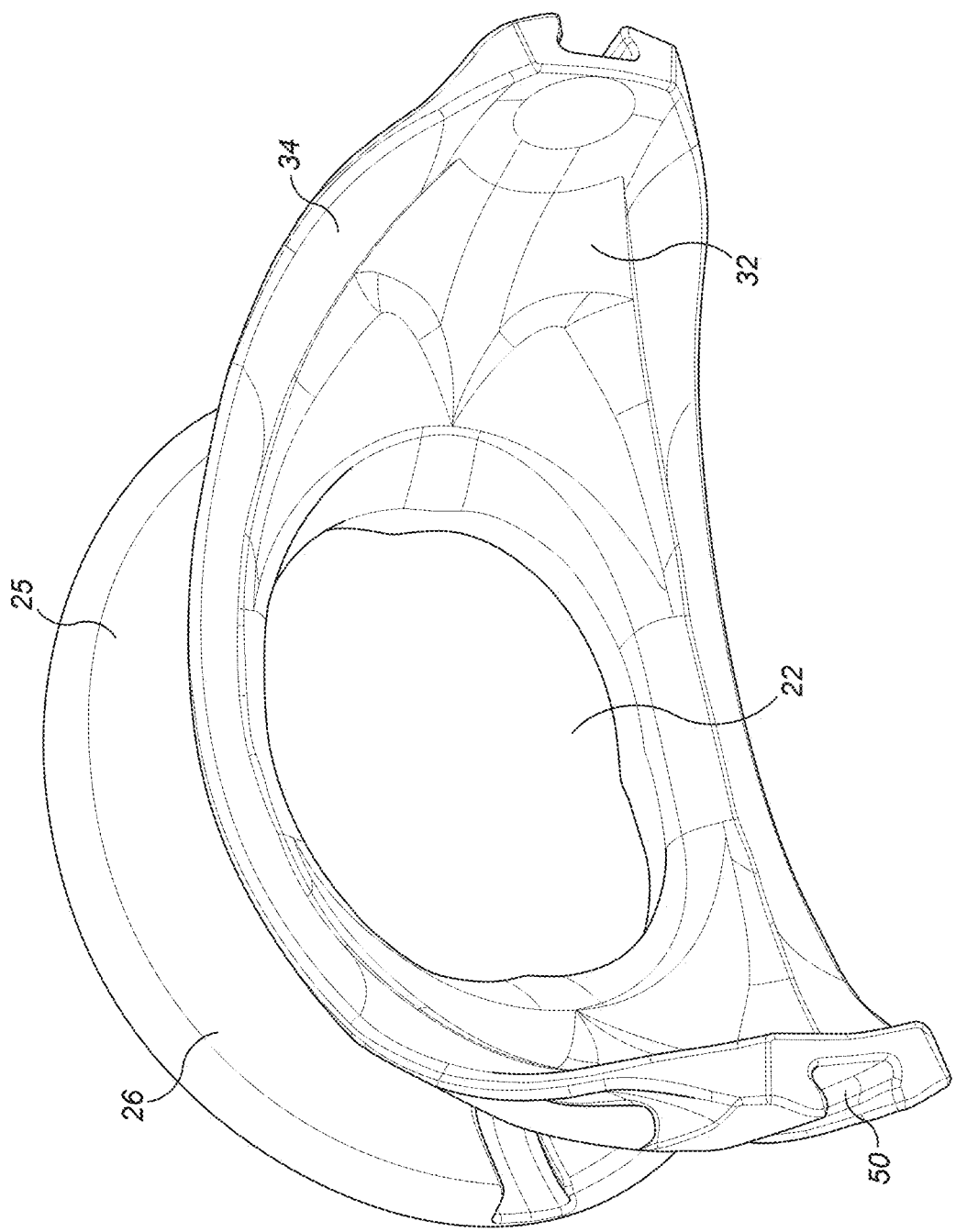
FIG. 4 is a rear perspective view of the dental retractor of FIG. 2.

The cheek retractor 30 will now be discussed in further detail with reference to FIGS. 2 to 4. As best shown in FIG. 3, the pair of distally extending arms 32 form an arch representative of a patient's dental arch. The arms 32 follow an arched path defined by a patient's dental arch. When the retractor 10 is positioned within a patient's mouth the arms 32 are located on the exterior of the dental arch, in the lower and upper labial sulcus of the patient. The arms 32 act as a barrier between the patient's cheek and dental arches thereby preventing the wet cheek contacting a patient's teeth during a dental procedure. The cheek retractor 30, and in particular the arms 32, promote outward movement of the patient's cheeks such that a gap is created between the internal surface of the patient's cheeks and dental arches. The distally extending arms 32 are configured to act as a cheek retractor 30 along the length of the lower and upper dental arches, from the front teeth to the back teeth, when the patient's mouth is both open and closed.

The skilled reader will appreciate that the term "depth" refers to the vertical or major dimension of the arched arms 32 and the term "thickness" refers to the horizontal or minor dimension of the arms 32.

As best viewed in the plan view of FIG. 3, the arms 32 define a continuous arch. The arms 32 extend distally from the lip retractor 20 and are connected to the annular body 24 of the lip retractor 20 at the point of inflexion of the arch, where the direction of the distally extending arms 32 changes. The annular body 24 of the lip retractor 20 extends proximally from the point of inflexion of the arch of the arms 32. The annular body 24 extends proximally to define a supporting surface upon which the patient's lips may rest such that they are supported and retracted by the supporting surface of the annular body 24. The annular body 24 and supporting surface may be circumferentially continuous around an opening or aperture extending through the annular body 24. A radially extending flange 26 extends radially from a proximal side of the annular body 24. The radially extending flange 26 defines a circumferentially continuous flange configured to engage and wrap around a patient's lips, in use. The annular body 24 and radially extending flange 26 may define, at least a portion of the lip retractor 20.

The arms 32 are tapered as they extend distally such that the depth of each arm 32 reduces as the arms 32 extend along the arched path. When the patient's mouth is open the vertical distance between the lower and upper arches is at a maximum in the region of the front teeth and reduces to a minimum in the region of the molars at the rear of the dental arch. As such, the taper of the arms 32 is representative of the angle formed by the lower and upper dental arches of a patient when their mouth is open. This beneficially improves the comfort of the retractor 10 and also ensures the cheeks are suitably retracted along the entire length of the dental arch.

The arms 32 further comprise lower and upper flanges 34 for contacting the palate or lingual sulcus of the mouth. The lower and upper flanges 34 are thinner than the body of the arms 32. This is beneficial as the flanges 34 are compliant to adapt to the shape of the soft tissue within a patient's mouth. This improves the comfort of the retractor 10 and also allows the retractor 10 to be used both when the patient's mouth is open and closed. When the patient closes their mouth they bite down on the flanges 34 of the arms 32 such that the flanges 34 deform and adapt to the shape of the patient's mouth when the mouth is closed. Similarly, when the patient's mouth is open, the flanges 34 mould to the inner lining of the mouth to ensure that the cheek remains suitably retracted and maintained away from the dental arches.

The upper and lower flanges 34 increase in length as the flange 34 extends distally along the arm 32 due to the tapered shape of the arm 32. The profile defined by the flanges 34 is representative of the profile of the lower and upper buccal sulcus within the mouth of the patient. As best viewed in FIG. 5, the taper of the arm 32 is representative of the angle formed by the lower and upper jaws when in an open position. This is beneficial as the arms 32 may retract a patient's cheek from the upper to the lower buccal sulcus when the patient's mouth is open. As mentioned above, the flanges 34 are thinner than the arms 32 and are thus deformable to mould to the soft tissue within a patient's mouth. This is beneficial as the cheek retractor may deform to mould to the soft tissue within the patient's mouth when the patient's mouth is both open and closed without causing discomfort to the patient.

The lower and upper flanges 34 are shorter in length at the front of the arms 32 compared to the rear of the arms 32. As such, the lower and upper flanges 34 are less compliant at the front of the cheek retractor 30 than at the rear of the cheek retractor 30. This is beneficial as it ensures that the patient's cheeks are retained in a position away from the patient's teeth at the front of the mouth, where the dentist accesses the patient's teeth, and beneficially is compliant at the rear of a patient's mouth to improve the comfort of the cheek retractor 30.

Figure 6:
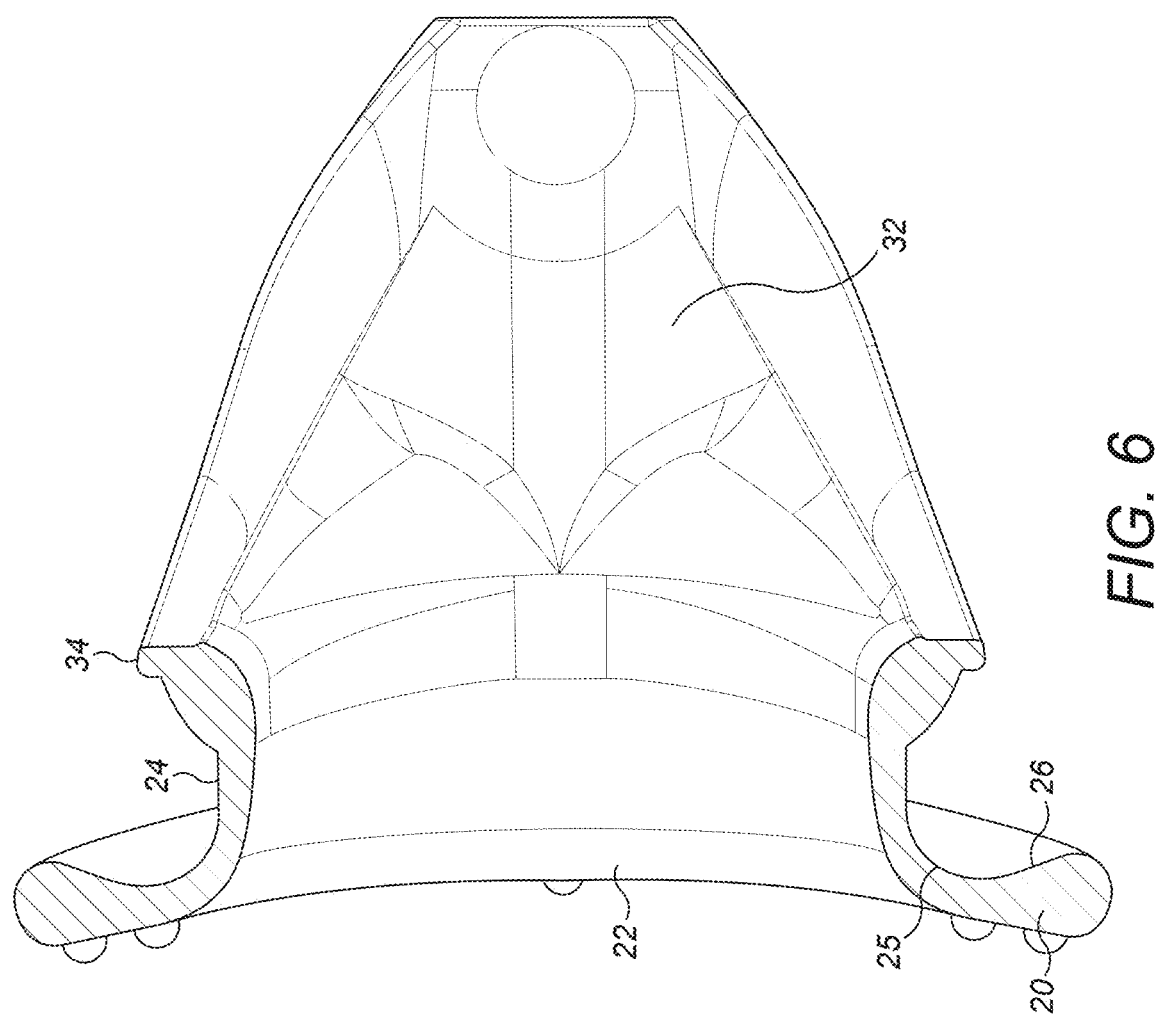
FIG. 6 is a cross-sectional side view of the dental retractor of FIG. 2.

As described, the arms 32 are arched and the lip retractor 20 is attached to the arms 32 in the region of inflexion of the arms 32. FIG. 6 shows a cross-sectional view of the retractor 10. An annular body 24 extends in a forward direction from the arms 32. The annular body 24 is a protrusion from the arms 32 defining a circumferential lip retractor 20 for controlling the position of a patient's lips. The lip retractor 20 supports the patient's lips and the ovoid shape of the patient's mouth. Beneficially, the circumferential lip retractor 20 facilitates multidirectional retraction of the lips thus providing unobstructed access to the patient's mouth. Furthermore, the arms 32, in the region of inflexion, promote movement of the patient's lips in a forward direction such that the lips rest on the annular body portion 24 away from the front teeth. As such, the arms 32 form part of the lip retractor 20 and define a gap between the patient's lip and front teeth. The arms 32 may be integral with or integrally attached to the lip retractor 20.

As mentioned above, when the retractor 10 is located within a patient's mouth the cheek retractor 30 is located within the patient's mouth such that the arms 32 spread the cheeks of the patient outward from the lower and upper dental arches. Similarly, the lips of the patient contact the circumferential lip retractor 20 and are promoted away from the front teeth onto the annular body 24 by the arched arms 32 to a retracted position. The skilled reader will appreciate that the retracted position is a position in which the lips do not obscure the patient's front teeth. The forwardly extending annular body 24 engages and supports the lips of a patient. The arms 32 promote forward movement of the lips, towards the annular body 24, as to define a gap between the patient's front teeth and lips. Access to the patient's mouth and teeth is then provided via the central aperture 22 of the retractor 10. The central aperture 22 extends through the annular body 24 and arms 32 such that an access is provided to the patient's teeth for the dentist.

The lip retractor 20 further comprises a radially extending flange 26 for locating the retractor 10 within a patient's mouth. The flange 26 surrounds and radially extends from the annular body 24. The flange 26 may be considered as an out-turned lip of the forwardly extending annular body 24. The out-turned lip or flange 26 transitions smoothly from the annular body 24 via a smooth radiussed curve 25. This is beneficial as the smooth curve 25 and flange 26 wraps around the exterior of the patient's lip, referred to as the vermillion, thereby locating the retractor 10 within the patient's mouth. As best viewed in FIG. 3, the flange 26 also has an arched profile in a plan view. The arched profile of the flange 26 represents the arched profile of a patient's face and lips. This is beneficial as it promotes contact between the flange 26 and the corners of the patient's mouth around the entire mouth opening.

As mentioned above, the arms 32 provide support to the patient's lip and promote forward movement of the lips in the region of inflexion of the arms 32 at the patient's front teeth. The arms 32 contact the upper and lower buccal sulcus in the region of the upper and lower buccal frenum. The internal surfaces of the lips of the patient are pushed in a forward direction by the arms 32 to create a gap. The gap created between the lips and the front teeth beneficially provides space for the dentist to perform dental procedures on the front teeth of the patient. The upper and lower flanges 34 of the arms 32 are relatively short in the region of the anterior teeth, however, the upper and lower flanges 34 are relatively thin and compliant as to provide a comfortable fit to the mucosa of the patient.

The arms 32 not only act as a cheek retractor 20 by providing support to the internal surface of the patient's cheeks but also further support and retract the patient's lips at the sides of the patient's mouth where the patient's cheeks meet their lips. As mentioned previously, the arms 32 follow the path of the dental arch and are located outboard of the patient's dental arch. As such, in the vicinity of the patient's front teeth where the patient's cheek meets their lip, the arms 32 and annular body simultaneously support and retract the patient's cheek and lips. The depth or vertical height of the arms 32 may be greater than the height of the annular body 24 in the region where the arms 32 are connected to the annular body 24 such that the arms 32 extend above and below the annular body 24.

Figure 7:
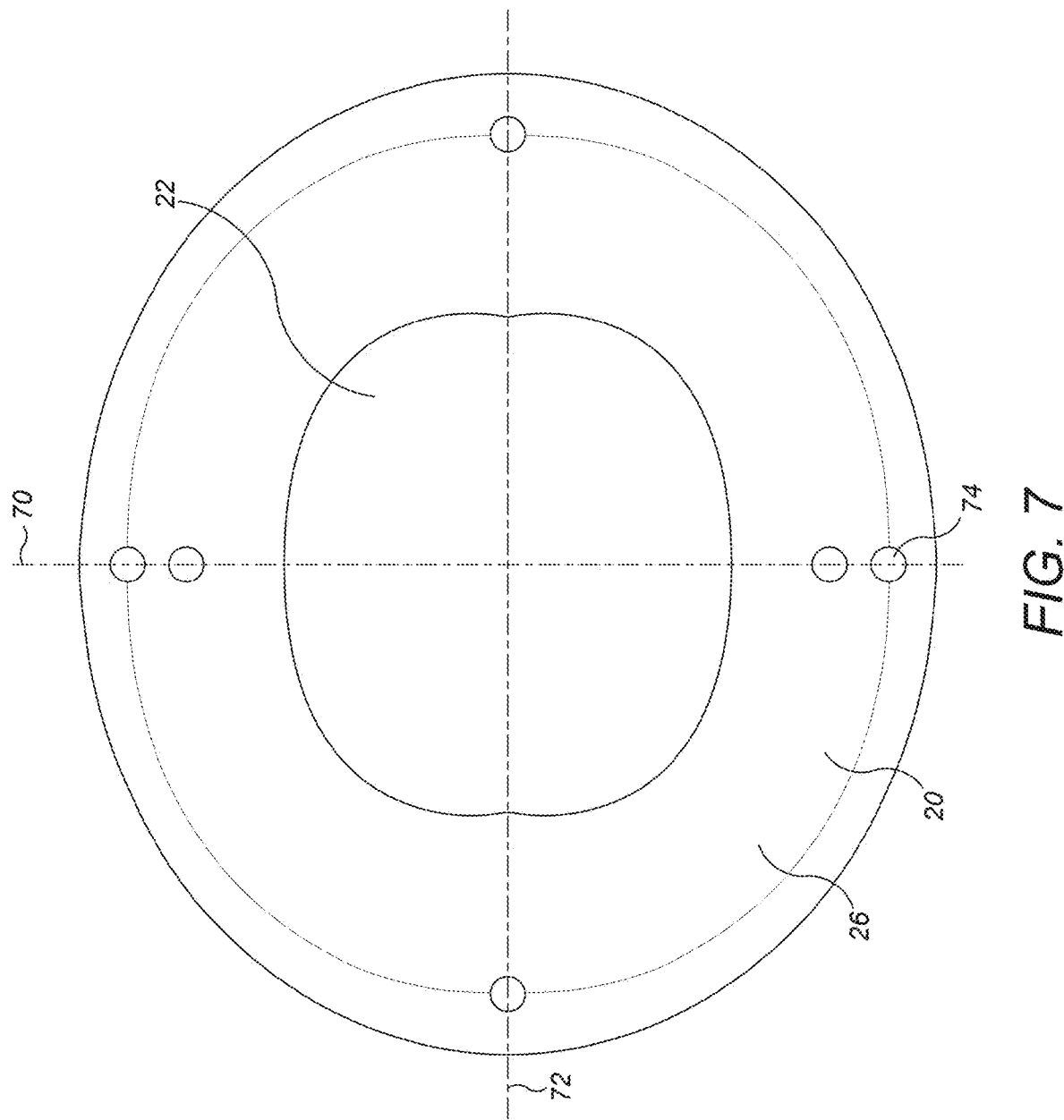
FIG. 7 is a front view of the dental retractor of FIG. 2.

FIG. 7 shows a front view of the retractor 10 with the tongue retractor 40 removed. The front surface of the lip retractor 20 comprises a plurality of embossed buttons or studs 74. The embossed buttons 74 are located along a central vertical axis 70 and a central horizontal axis 72. Beneficially, the embossed buttons 74 provide the dentist with a visual reference aid that represents the vertical axis 74 and the horizontal axis 72. The buttons 74 located on the vertical axis 70 provide the dentist with a line of symmetry of the vertical midline of a patient's mouth. It may be helpful in certain dental procedures for the dentist to see a marked centre line that is easy to identify and is a visual reference marker on saved images of the patient's mouth or during a dental procedure. Similarly the reference buttons on the horizontal axis 72 provide a visual reference for the central horizontal axis 72 which is useful when measuring the occlusal plane and variations.

Furthermore, the buttons 74 may provide an indication as to the size of the retractor 10. Patient's mouths are different sizes and as such it may be desirable to provide different sizes of retractor 10 to fit each patient. For example, the retractor 10 may come in three different sizes and the number of buttons 74 may represent the size of the retractor 10. In the example shown in FIG. 7, there are two buttons 74 located on the vertical plane 70 which may be indicative of a size two out of, for example three sizes. The skilled reader will appreciate that any number of size variations may be implemented and indicated by the buttons 74 or any other mark on the retractor accordingly.

Figure 8:
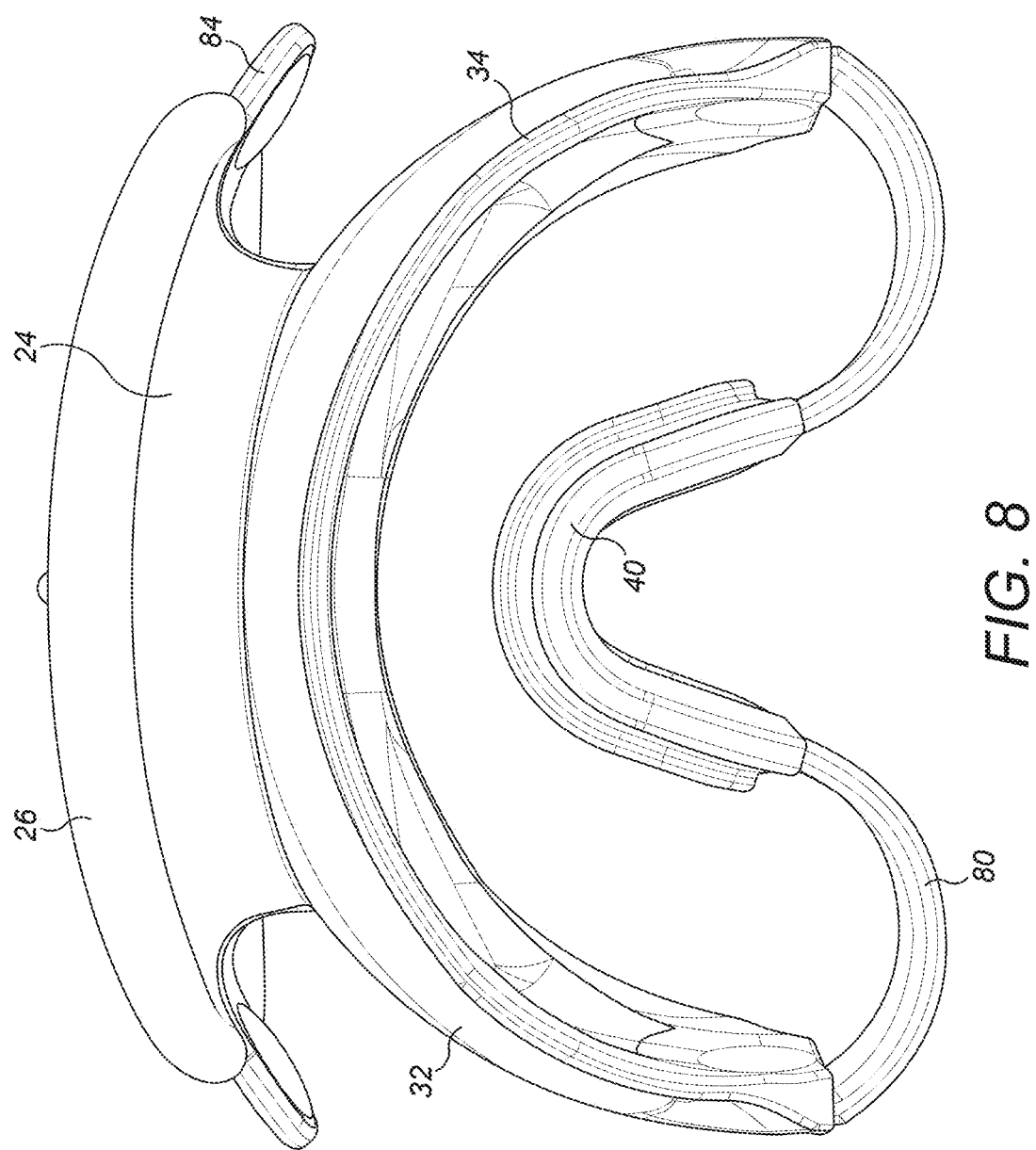
FIG. 8 is a plan view of the dental retractor of FIG. 1 with the tongue retractor attached.

Turning to FIG. 8, the removable tongue retractor 40 is shown when secured to the retractor 10. The tongue retractor 40 comprises a U-shaped tongue retractor 40 for retaining the patient's tongue towards the rear of their mouth during a dental procedure. The U-shape of the tongue retractor 40 is shaped to match the arch of the lingual surfaces of the arch form of the tongue. The tongue retractor 40 may be a soft sheet of medical grade silicone. The top and bottom edges of the tongue retractor 40 are thinner than the main body portion and are thus more compliant and deformable than the centre of the tongue retractor 40. This is beneficial as the bottom and top of the tongue retractor 40 contacts the floor and ceiling of the mouth and is deformable as to adapt to the shape of the patient's mouth. This is particularly advantageous when the patient is required to open or close their mouth during a procedure. The soft silicone of the tongue retractor 40 is deformable so as to adapt to the shape, and to maintain contact with, the floor and ceiling of the patient's mouth both when the mouth is open and closed.

As shown in FIG. 8, the central portion of the tongue retractor 40 is made from a thicker silicone material. This is advantageous as the thicker material provides additional strength and rigidity to the tongue retractor 40 in the region of the tongue retractor 40 that contacts a patient's tongue.

Figure 9:
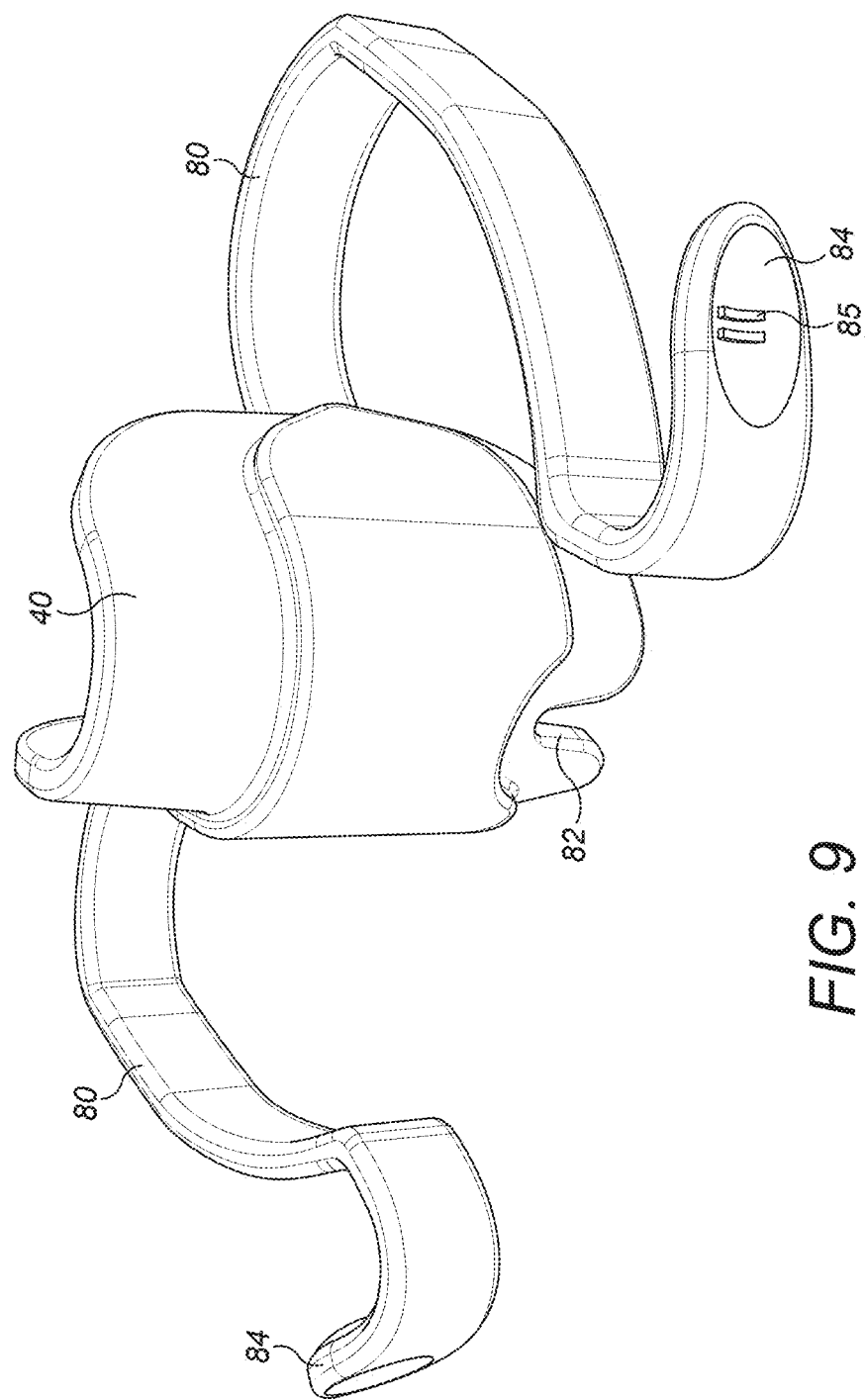
FIG. 9 is a perspective view of a tongue retractor according to an embodiment of the invention.
Figure 10:
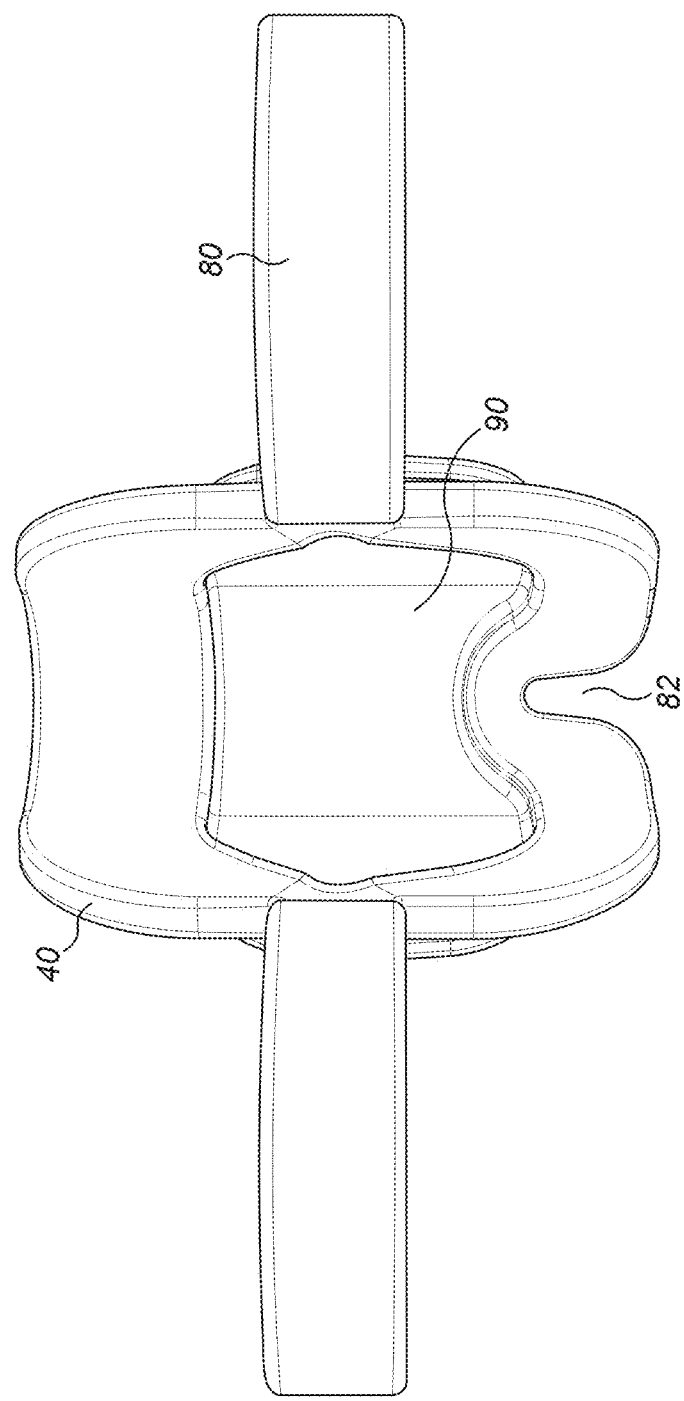
FIG. 10 is a rear view of the tongue retractor of FIG. 9.

FIGS. 9 and 10 show a front perspective view and a rear view of the tongue retractor 40 respectively. The tongue retractor 40 comprises a notch 82 positioned on the bottom surface of the tongue retractor 40. The notch 82 is configured to accommodate the lingual frenum of the tongue when the patient's tongue is retained by the tongue retractor 40. The groove or notch 82 is dimensioned so as to accommodate and provide a clearance gap around the lingual frenum thereby improving the comfort of the tongue retractor 40 and reducing the gag reflex of the patient.

Turning to FIG. 10, the tongue retractor 40 comprises a recess 90 located on the distal side of the tongue retractor 40 to accommodate the tip of the tongue. Furthermore, the recess 90 helps to retain the tongue behind the tongue retractor 40. The variations in thickness of the tongue retractor are radiussed so as to provide a smooth surface to contact the patient's tongue. This is beneficial as the smooth surfaces improve the overall comfort of the tongue retractor 40 and further reduces the gag reflex of the patient.

The tongue retractor 40 further comprises two straps 80 or attachment means extending laterally from the tongue retractor 40 for attaching the tongue retractor 40 to the retractor 10. The straps 80 are moulded from the soft silicone material of the tongue retractor. As such, the tongue retractor 40 and straps 80 may be made from a single moulded silicone component.

Figure 5:
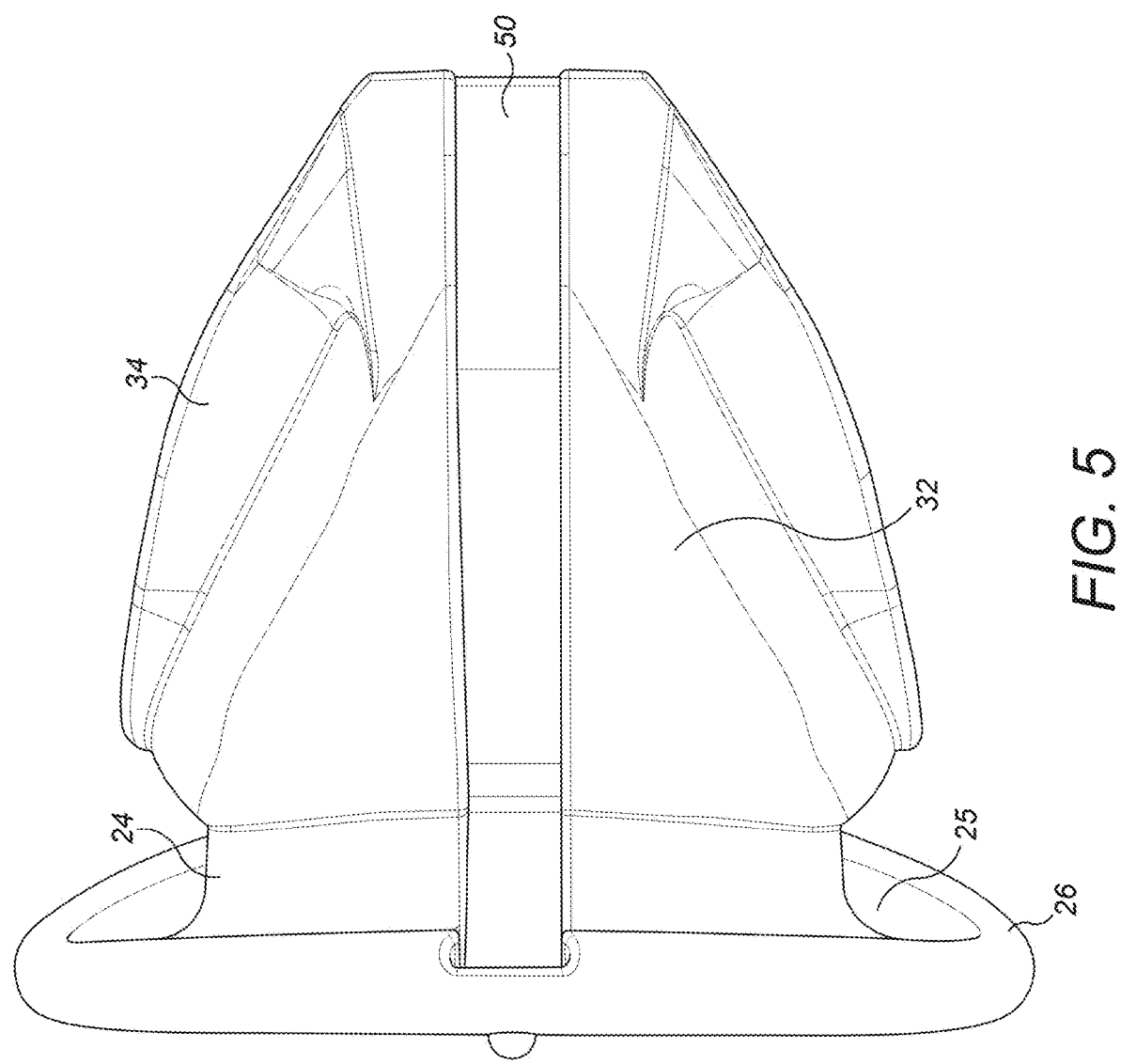
FIG. 5 is a side view of the dental retractor of FIG. 2.

The straps 80 are configured to engage a corresponding channel 50 defined on the external surface of the retractor 10. As shown in FIGS. 4 and 5, the channel 50 extends in a fore-aft direction along the external surface of the arms 32, annular body 24 and flange 26 of the retractor 10 to form a continuous groove. A channel 50 extends along the external surface of both the arms 32.

The tongue retractor 40 is coupled to the retractor 10 by the straps 80. The straps 80 are dimensioned such that they are a transition or interference fit with the channel 50 to provide a snap fit between the channel 50 and the strap 80. As such the friction between the strap 80 and channel 50 retains the strap 80 within the channel 50 and thus secures the tongue retractor 40 to the retractor 10.

Figure 11:
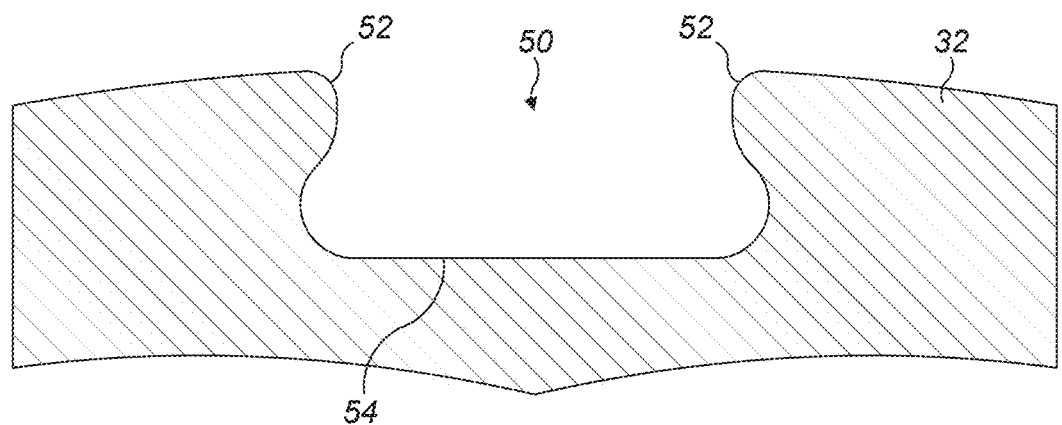
FIG. 11 is a cross-sectional view of a channel for attaching the tongue retractor to the dental device.
Figure 12:
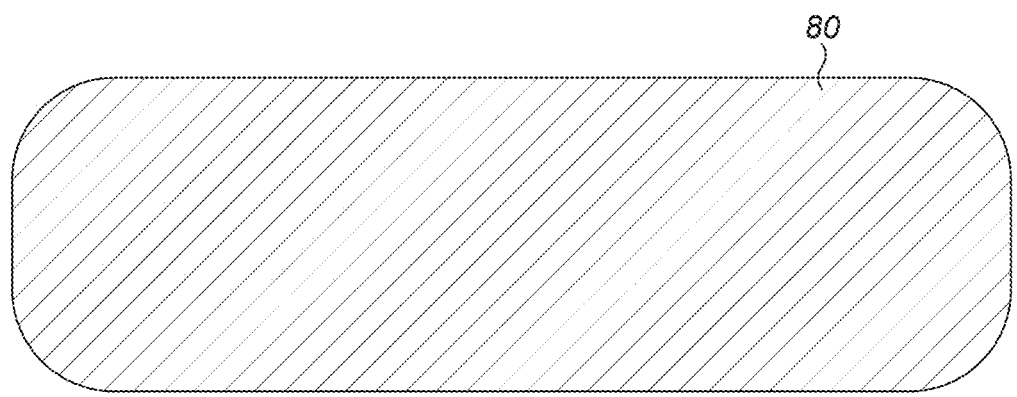
FIG. 12 is a cross-sectional view of a strap on the tongue retractor element.

FIG. 11 and FIG. 12 show cross-sectional views of the channel 50 and the strap 80 respectively. The channel 50 comprises a pair of over-hanging lips 52 located on opposing sides of the channel 50. The over-hanging lips 52 define the entrance to a cavity 54 within the channel 50. The entrance to the cavity 54 is narrower than the base of the channel 50. This is advantageous as the over-hanging lips 52 provide a snap-fit attachment when locating the strap 80 within the channel 50 and prevent the straps 80 from inadvertently being dislodged from the channel 50. As shown in FIG. 12, the cross-sectional profile of the strap 80 is substantially rectangular with rounded or filleted corners. The strap 80 is dimensioned to be retained within the cavity 54 in the base of the channel 50. The rounded corners of the strap 80 make it easier to locate the strap 80 within the channel 50.

As shown in FIG. 1, FIG. 8 and FIG. 9 the strap 80 comprises a tab 84 at the end of each strap 80. The tab 84 provides a grip that a dentist may use to adjust the position of the strap 80 and thus tongue retractor 40 relative to the retractor 10. As described above, when the tongue retractor 40 is secured to the dental retractor 10 the strap 80 is located within the cavity 54 of the channel 50. The strap 80 is retained within the channel 50 by the over-hanging lips 52 which prevent the strap 80 from being removed from the channel 50. However, advantageously the over-hanging lips 52 allow the strap 80 to be slid along the length of the channel 50 relative to the retractor 10. As such, a dentist may grip the tab 84 and pull the strap 80 through the channel 50 to control the position of the tongue retractor 40 within a patient's mouth.

Pulling the tab 84 and thus strap 80 pulls the tongue retractor 40 in a forward direction and thus enables the dentist to control the position of a patient's tongue within their mouth. Furthermore, the dentist may pull one tab 84 at a time thereby pulling the tongue retractor 40 in a lateral direction relative to the retractor 10. This is beneficial as it allows the dentist to centre the tongue retractor 40 within a patient's mouth and also to control the distance the tongue is retracted by. This improves the level of comfort to the patient and helps minimise the gag reflex of the patient.

As shown in FIG. 9, the tab 84 comprises a pair of embossed ridges or grips 85. The grips 85 serve two primary functions. Firstly, the raised profile makes the tabs 84 easier to grip and thereby position relative to the contractor 10. Secondly, the number of embossed ridges 85 represents the size of the tongue retractor 40. The size of the tongue retractor 40 corresponds to the size of the retractor 10 as indicated by the buttons 74. As such a dentist may easily select the correct size of tongue retractor 40 to be fitted to the retractor 10. In the example in FIG. 9, the tab 84 comprises two ridges 85 indicative of a size two as also indicated by the buttons 74 in FIG. 7.

The retractor 10 may be made from soft medical grade silicone. The soft silicone material advantageously provides a level of the compliance to the retractor 10. The compliance of the soft silicone improves the comfort of the retractor 10 as it may deform and fit to the patient's mouth. The soft silicone is resilient such that the shape of the retractor 10 is retained. Furthermore, the medical grade silicone is autoclavable and thus easily sterilised and re-used. The skilled reader will appreciate that an alternative material may be used. For example, a plastics material may be used and the retractor 10 may be disposable after use.

The dental retractor 10 may be used with or without the tongue retractor 40 depending on the procedure being performed by the dentist. When positioning the retractor 10 within a patient's mouth the dentist may squeeze the retractor 10 to temporarily reduce the height of the retractor 10 thereby making it easier to locate within a patient's mouth. In particular, the dentist may squeeze the lip retractor 20 and annular body 24 to aid fitting the retractor 10 within the patient's mouth. When the dentist is satisfied that the retractor 10 is in approximately the correct location within a patient's mouth the dentist may relieve the pressure on the lip retractor 20, thereby allowing the retractor 10 to expand to it's original shape and mould to the shape of the patient's mouth.

As the retractor 10 returns to its original shape the flange 26 on the lip retractor 20 may contact the outer surface of the patient's lips. This is beneficial as the flange 26 further improves the location of the retractor 10 within the patient's mouth and ensures that the retractor 10 is correctly positioned. When the retractor 10 is in position within the patient's mouth the dentist may adjust the position of the tongue retractor 40, if secured to the retractor 10, by pulling on the tabs 84 to adjust the length and position of the straps 80 relative to the retractor 10. This is beneficial as the dentist may adjust the tongue retractor 40 prior to commencing a dental procedure to ensure the patient is not experiencing any discomfort. Furthermore, the dentist can ensure the soft tissue of the patient's mouth is positioned appropriately prior to commencing the procedure.

Figure 13:
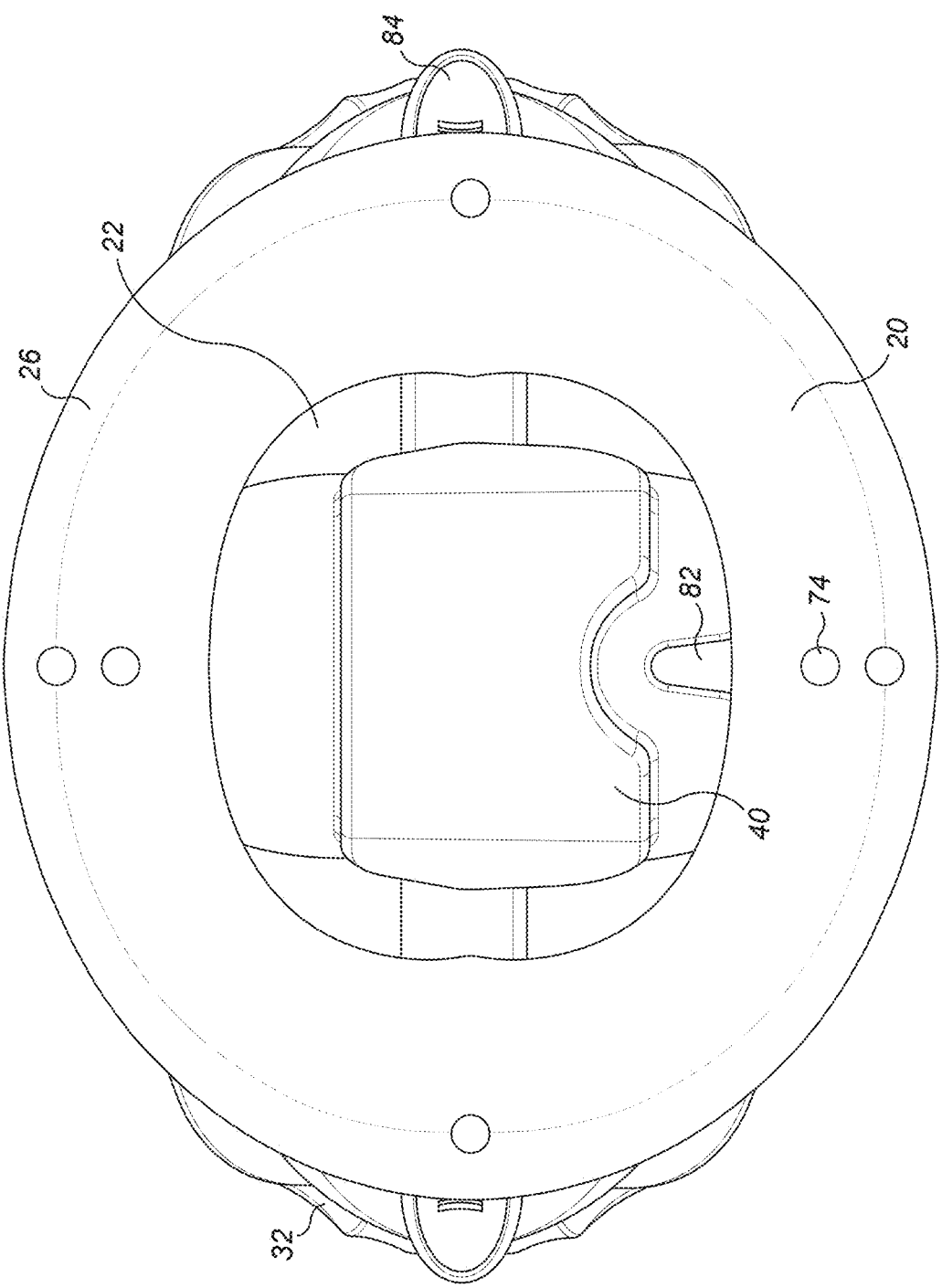
FIG. 13 is a front view of the dental retractor of FIG. 1.
Figure 14:
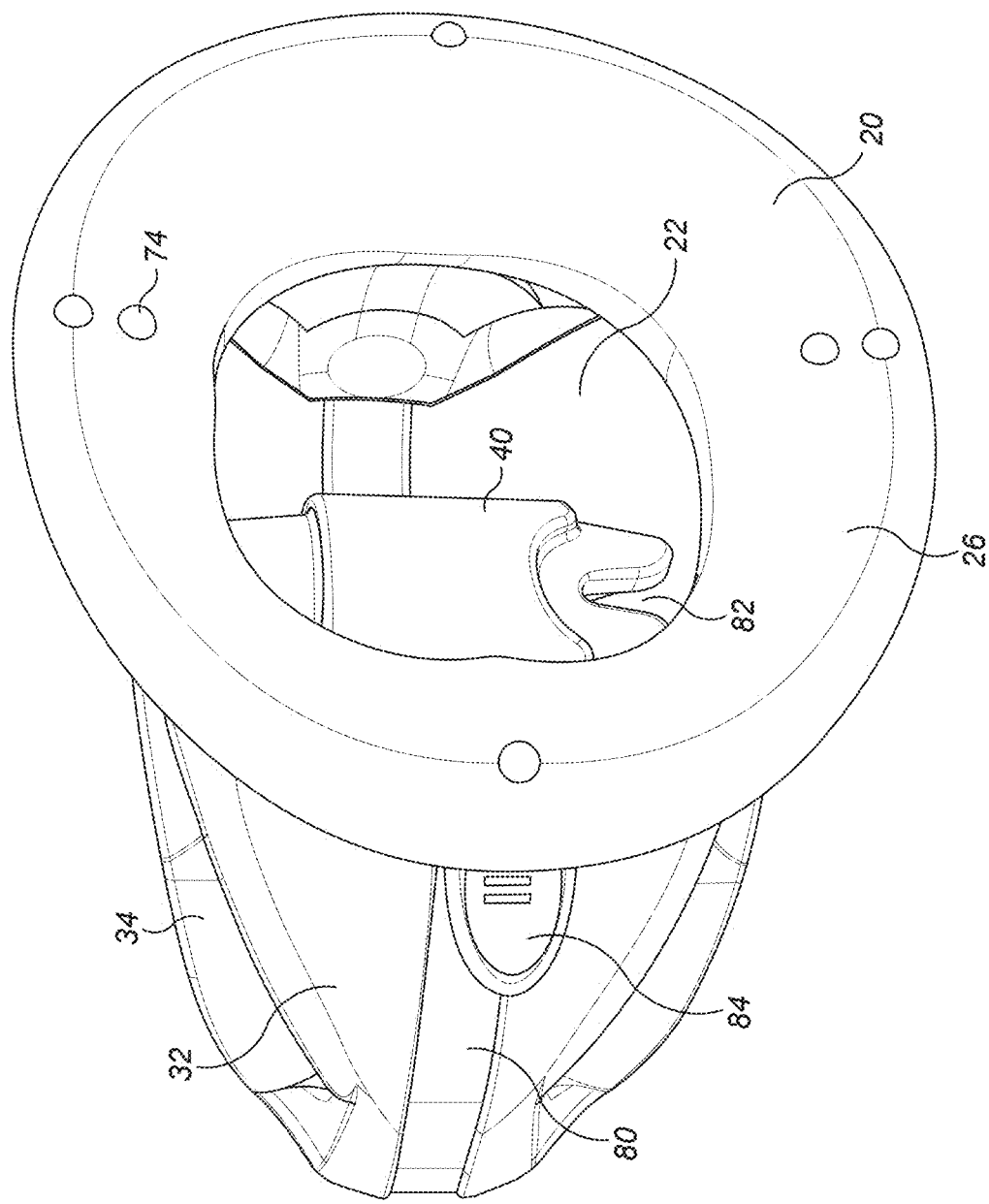
FIG. 14 is a front perspective view of the dental retractor of FIG. 1.

FIG. 13 and FIG. 14 show a front view and front perspective view of the retractor 10 and the tongue retractor 40 respectively. The retractor 10 may be made from a black material, for example matt black medical grade silicone. This is beneficial as the retractor 10 may also be used as a dental contraster for photographing a patient's teeth. As such, the views shown in FIG. 13 and FIG. 14, representative of the view the dentist may have when the retractor 10 is fitted to a patient's mouth, shows how the retractor 10 covers the soft tissue within a patient's mouth such that the teeth are contrasted against a black background. The dentist may simultaneously photograph the lower and upper dental arches when the patient's mouth is open or closed due to the compliant retractor 10.

As shown in FIG. 14, the arm 32 and tongue retractor 40 define a passage within which the patient's lower and upper dental arches may be located, in use. The tongue retractor 40 and arms 32 define walls of the passage and prevent the soft tissue of the patient's mouth encroaching into the passage and potentially obstructing the dentist during a dental procedure. The walls of the passage for the lower and upper dental arches cover the soft tissue within the patient's mouth. As such, a dark background is provided by the retractor 10 and tongue retractor 40 against which the patient's teeth may be photographed. This is advantageous as the retractor 10 may be fitted within a patient's mouth to retract the soft tissue whilst also acting as a contraster. This mitigates the requirement to fit separate retractor components and contrasters within the patient's mouth as these are difficult to position and may cause discomfort to the patient.

Further embodiments are now described with reference to FIGS. 15 to 19 in which the dental retractor 10 is shown for use with an elastomeric sheet 150 removably secured to the dental retractor 10. The sheet 150 or skin (referred to in the profession as a "rubber dam") may be used to shield an operative site, for example a tooth, from the cavity of the patient's mouth having an oral environment of saliva such that the dentist may perform a procedure on the operative site without debris from the procedure falling into the patient's mouth. Furthermore, the sheet 150 may be used to locate or suspend an endoscope during an endoscopy procedure. For clarity reference numerals for equivalent features have been kept constant for ease of reference when describing the further embodiments.

In general terms, an elastomeric sheet 150 or skin may be secured to the dental retractor 10 such that the sheet 150 extends over at least a major portion front surface 152 of the dental retractor 10. The dental retractor 10 acts as a frame to support and retain the sheet 150 in position during a procedure such as a dental procedure or an endoscopy. After the procedure the dentist may remove the sheet 150 such that the retractor 10 can be sterilised and a new sheet 150 or rubber dam may be fitted for use with another patient.

Figure 15:
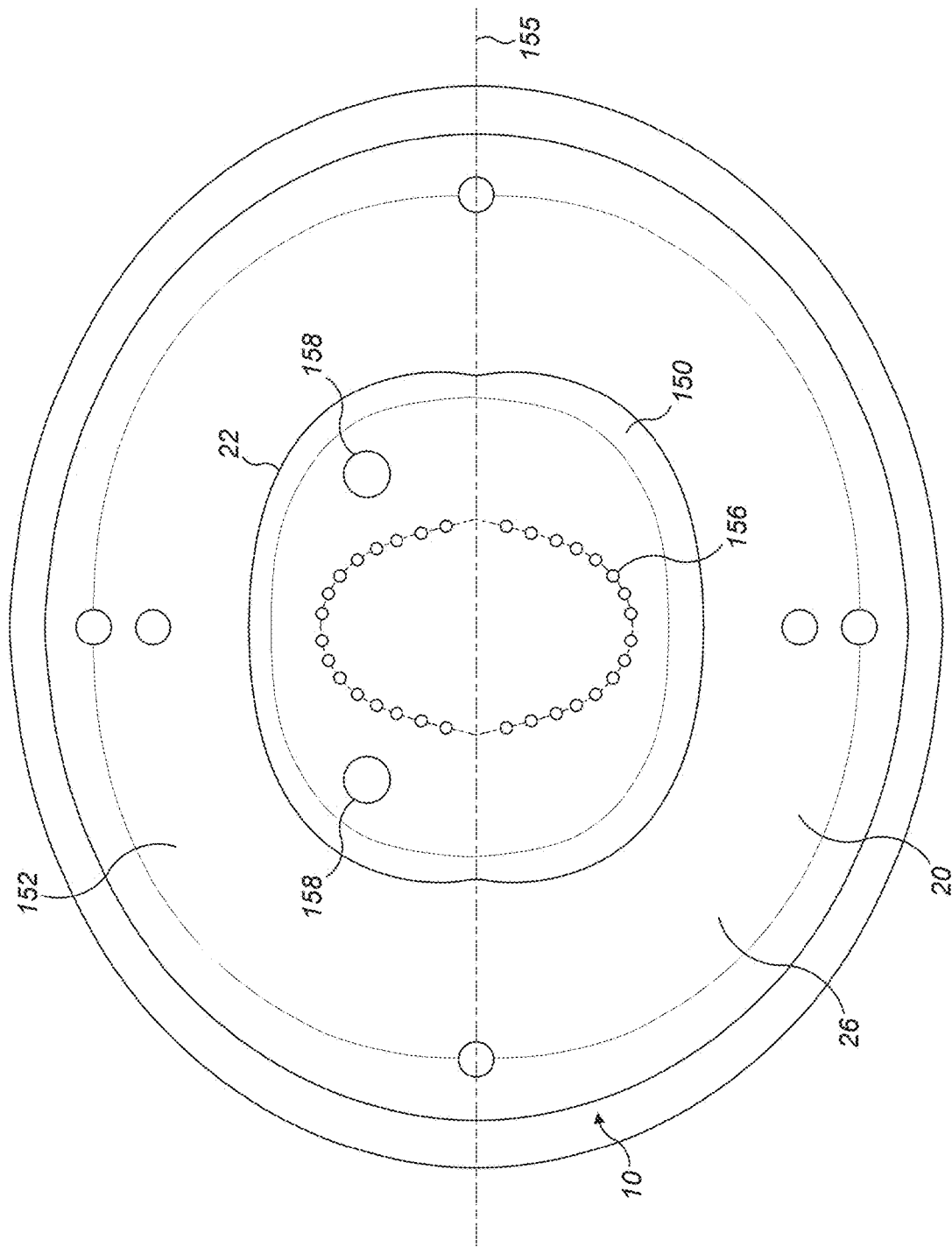
FIG. 15 is a front view of the dental retractor comprising a sheet according to another embodiment of the invention.

FIG. 15 shows a front view of the dental retractor 10 fitted with a rubber or silicon sheet 150 secured to the lip retractor 20 for use during dental procedures. For illustrative purposes the sheet 150 is shown as being transparent such that the dental retractor 10 is visible in FIG. 15. The sheet 150 is configured to act as a rubber dam to seal an operative site, such as a tooth, from the rest of the mouth thereby allowing the dentist to perform a dental procedure on the tooth. The sheet 150 is a thin, elastomeric sheet configured to act as a barrier between the operative site, for example one or more teeth, and the inner tissue of the patient's mouth. The sheet 150 is removably coupled to the dental retractor 10 such that the sheet 150 may be easily removed and disposed of after use.

The sheet 150 is secured to the dental retractor 10 such that it extends over at least a major portion of the front surface 152 of the dental retractor 10. The sheet 150 may wrap around the radially extending flange 26 of the lip retractor 20 so as to grip the lip retractor 20 and secure the sheet 150 to the lip retractor 20. As best viewed in FIG. 16, a portion of the sheet 150 may be received within the central aperture 22 when the sheet 150 is secured to the front surface 152 of the dental retractor 10. The sheet 150 may be dimensioned such that there is excess or slack material in the sheet 150 that allows the sheet to be received within the central aperture 22. Alternatively, the sheet 150 may be formed so as to have residual stiffness such that the sheet 150 is a generally dome shape. The domed portion of the sheet 150 may be received within the central aperture 22.

Figure 16:
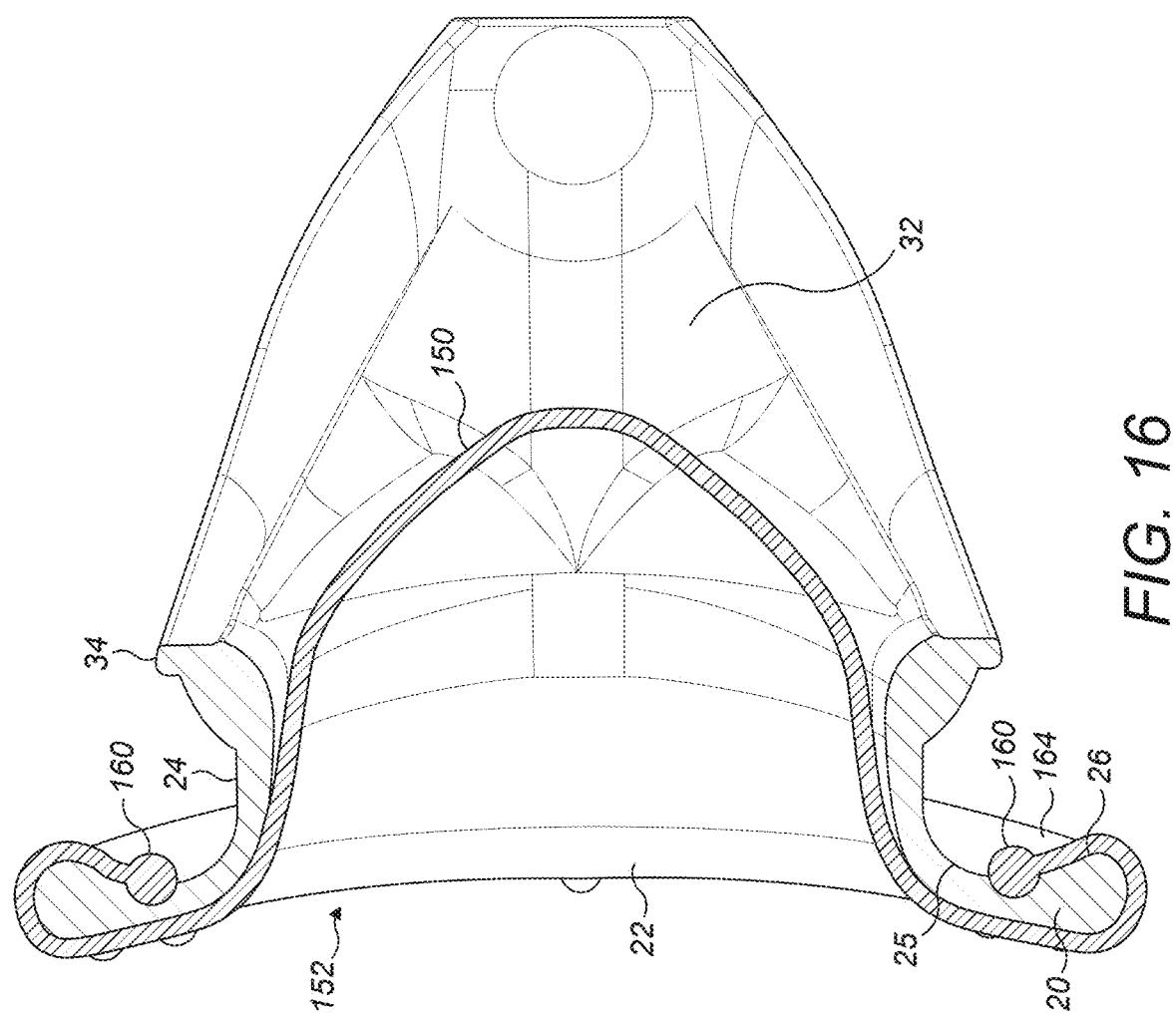
FIG. 16 is a cross-sectional side view of the dental retractor and sheet of FIG. 15.

FIG. 16 shows a cross-sectional side view of the dental retractor 10 and sheet 150 of FIG. 15. As mentioned above, the sheet 150 is at least partially received within the central aperture 22 of the dental retractor 10. This is beneficial as the portion of the sheet 150 received within the central aperture 22 generally follows the internal profile of the patient's mouth such that the sheet at least partially contacts the top and bottom teeth of the patient. This is beneficial as the dentist may make one or more holes in the sheet 150 corresponding to the position of the teeth that the dental procedure is to be performed on. When the dental retractor 10 and sheet 150 are positioned within a patient's mouth the dentist may easily stretch the hole in the sheet 150 over the operative site so as to place the tooth within the hole to create a seal around said tooth.

As shown in FIG. 15, the sheet 150 comprises a series of indicators 156 to indicate the position of each tooth within a patient's mouth. The indicators 156 may be printed marks, raised bumps or the like to indicate the position of each tooth within the patient's mouth. Prior to performing a dental procedure, the dentist may use a punch to create holes in the sheet 150 corresponding to the one or more teeth that the dental procedure relates to. When the dental retractor 10 is positioned in a patient's mouth the dentist may press the one or more holes over the operative site or sites within the mouth such that the tooth protrudes through the hole in the sheet 150 when the retractor 10 is positioned within the patient's mouth. The elastomeric sheet 150 can stretch such that the holes may expand to accommodate a tooth within the corresponding hole. This can then be secured over the tooth with a rubber dam clamp or the like. This is beneficial as the sheet 150 acts as a barrier or a dam between the tooth and the patient's mouth.

Furthermore, the sheet 150 may comprise one or more apertures 158. The apertures 158 act as air holes to allow the patient to breathe through their mouth when the dental retractor 10 and sheet 150 is positioned within their mouth. As shown in FIG. 15 the sheet 150 may comprise two apertures 158 such that one aperture 158 may act as a breathing hole and the other aperture 158 may allow a saliva ejector to be positioned within the patient's mouth to prevent the build-up of saliva within the patient's mouth during a procedure. The apertures 158 may be laterally offset from a central horizontal axis 155. This is beneficial as the sheet 150 may be secured to the dental retractor 10 such that the apertures may be off set above the horizontal axis 155 such that the apertures 158 are proximal to the upper dental arch of the patient. Alternatively, the sheet 150 may be rotated 180° such that the apertures 158 are proximal to the lower dental arch. In a further embodiment the sheet 150 may have four apertures 158 with two apertures 158 located on opposing sides of the horizontal axis 155.

As shown in FIG. 16, the sheet 150 further comprises a bead 160 or rim that extends along the peripheral surface of the sheet 150. The bead 160 may comprise an elastomeric cord such that the bead 160 can be stretched so as to fit around the outer surface or flange 26 of the lip retractor 20 thereby gripping the flange 26 and retaining the sheet 150 on the dental retractor 10. The bead 160 may engage a retention formation, for example a groove 162, positioned on a rear surface 164 of the lip retractor 20. For example, the retention formation may be positioned on a rear surface of the flange 26. When the bead 160 of the sheet 150 is positioned on the rear surface 164 of the lip retractor 20 the bead 160 may contract so as to engage the lip retractor 20 or retention formation or groove 162 and secure the sheet 150 over the front face 152 of the dental retractor 10. The sheet 150 is easily secured to, and removed from, the dental retractor 10 by a dentist by stretching the bead 160 so as to disengage the bead 160 from the dental retractor 10.

Figure 17:
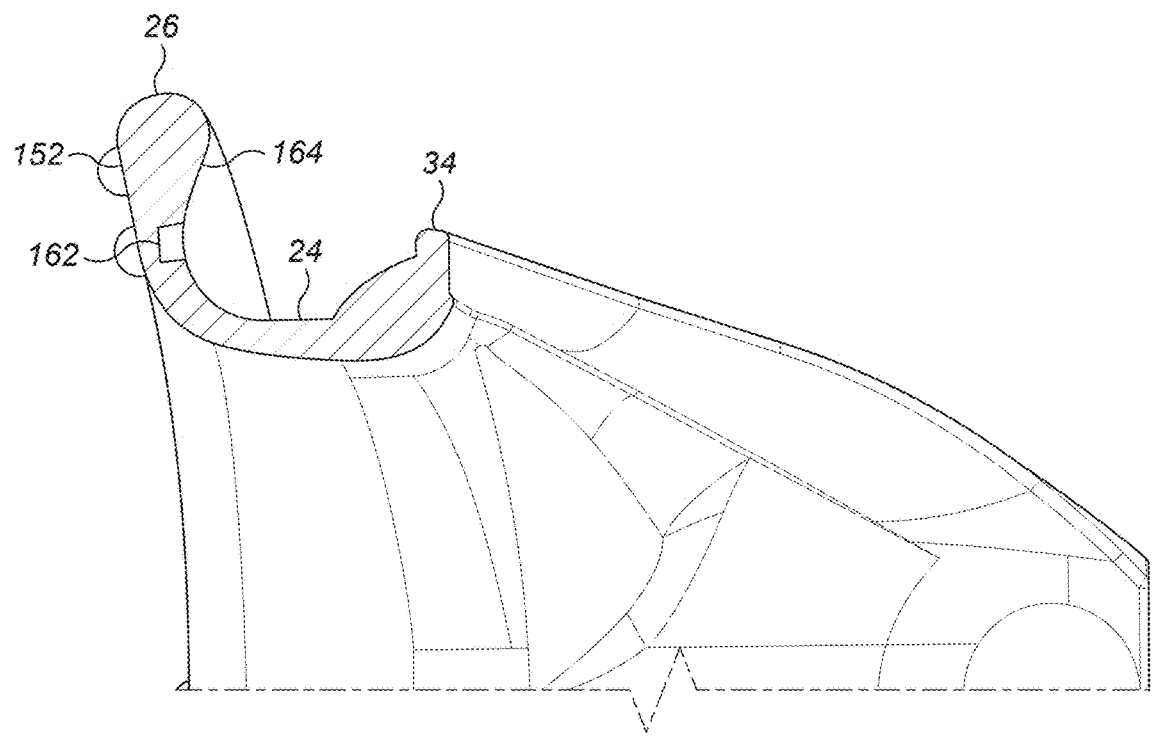
FIG. 17 is an enlarged cross-sectional side view of the dental retractor of FIG. 15.

FIG. 17 shows an enlarged cross-sectional side view of the lip retractor 20 and groove 162 positioned on the rear surface 164 of the flange 26 of the lip retractor 20. The groove 162 is an example of a retention formation that is configured to at least partially receive the bead 160 of the sheet 150 such that the bead 160 may be located and retained within the groove 162. The groove 162 extends around the rear surface 164 of the lip retractor 20. However, in another embodiment the groove 162 or retention formation may be positioned on the annular body 24. The skilled reader will understand that whilst the example illustrated in the figures exemplifies the retention formation as a groove 162, the retention formation may be a ridge, a raised protrusion, a hook or a series of raised protrusions.

Figure 18:
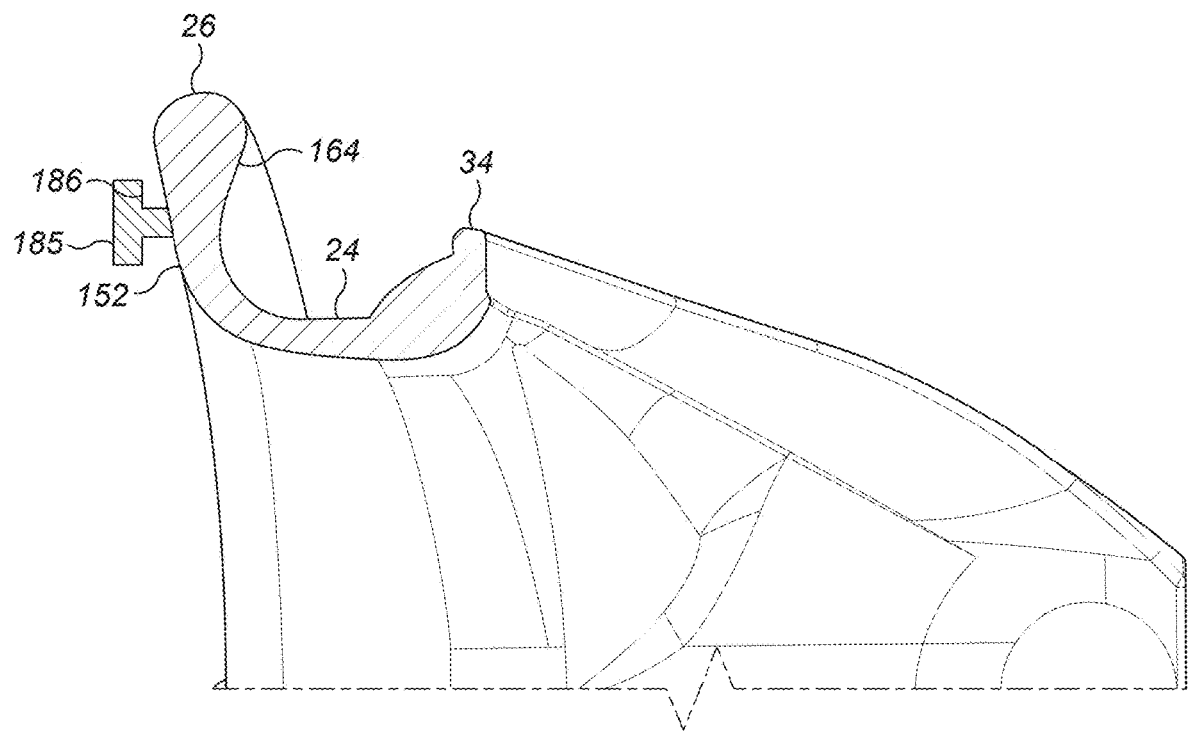
FIG. 18 is an enlarged cross-sectional side view of the dental retractor of FIG. 15 according to another embodiment of the invention.

FIG. 18 shows another embodiment in which a series of raised protrusions 185 or formations may extend from the front surface 152 of the dental retractor 10. The raised protrusions 185 may be configured to engage the bead 160 of the sheet 150 such that sheet 150 is hooked or gripped thereby securing the sheet 150 to the front surface 152 of the dental retractor 10. The raised protrusions may be raised hooks or retaining features configured to grip and retain the bead 160 of the sheet 150 between a gripping surface 186 of the raised protrusion and the front surface 152 of the dental retractor 10. Placing the retention formations on the front surface 152 is beneficial as it allows the easy placement and removal of the sheet 150 when the retractor 10 is in the patient's mouth.

The dental retractor 10 beneficially controls the position of the patient's cheeks and lips during a procedure thereby increasing the space in which the dentist may perform the procedure. Furthermore, the sheet 150 acts as seal or dam between the operative site and the rest of the patient's mouth. This beneficially allows the dentist to work on the operative site without saliva contacting the operative site and furthermore prevents debris from the procedure falling into the patient's mouth. At the end of the procedure the dentist may simply remove the sheet from the operative site and remove the entire dental retractor 10 and sheet 150 assembly from the patient's mouth. This prevents any debris gathered on the sheet 150 from falling into the patient's mouth after the procedure has been completed.

Figure 19:
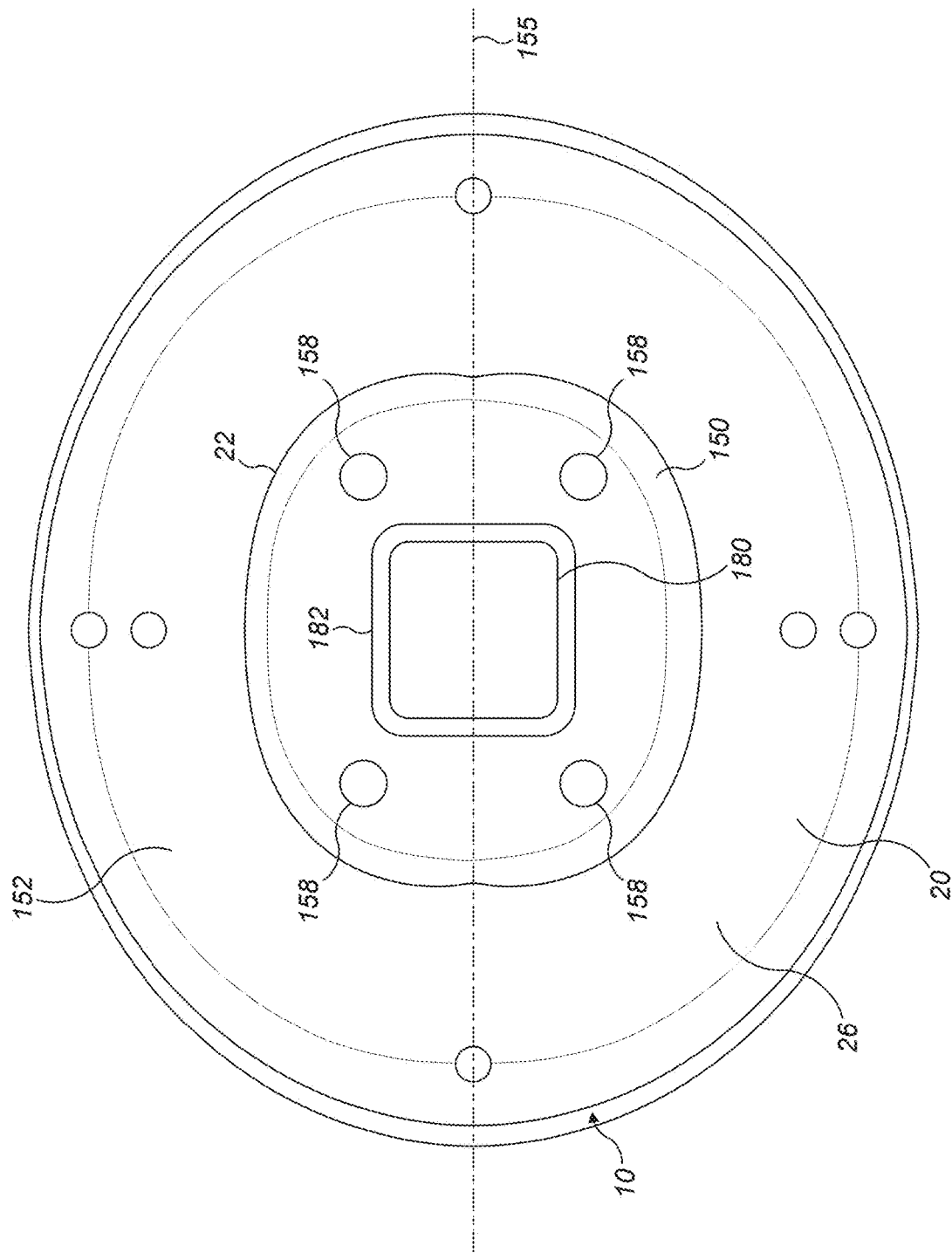
FIG. 19 is a front view of the dental retractor comprising a sheet according to another embodiment of the invention.

Turing now to FIG. 19, another embodiment of the invention is exemplified for use with an oral endoscope. In general terms, a sheet or skin 150 is secured to the dental retractor 10, as described above, and the sheet 150 comprises an aperture 180. The aperture 180 is configured to receive an endoscope during an endoscopy procedure so as to support the endoscope during the procedure and to protect it from the patient's teeth. The endoscope may be received within a hard plastics mouthpiece 190 (not shown in FIG. 19) which is received within the central aperture 180 and supported by the elastomeric sheet 150. The mouthpiece comprises a channel 196 for receiving the endoscope during an endoscopy procedure. The sheet 150 has been illustrated as being transparent in FIG. 19 such that the dental retractor 10 is visible.

Figure 20:
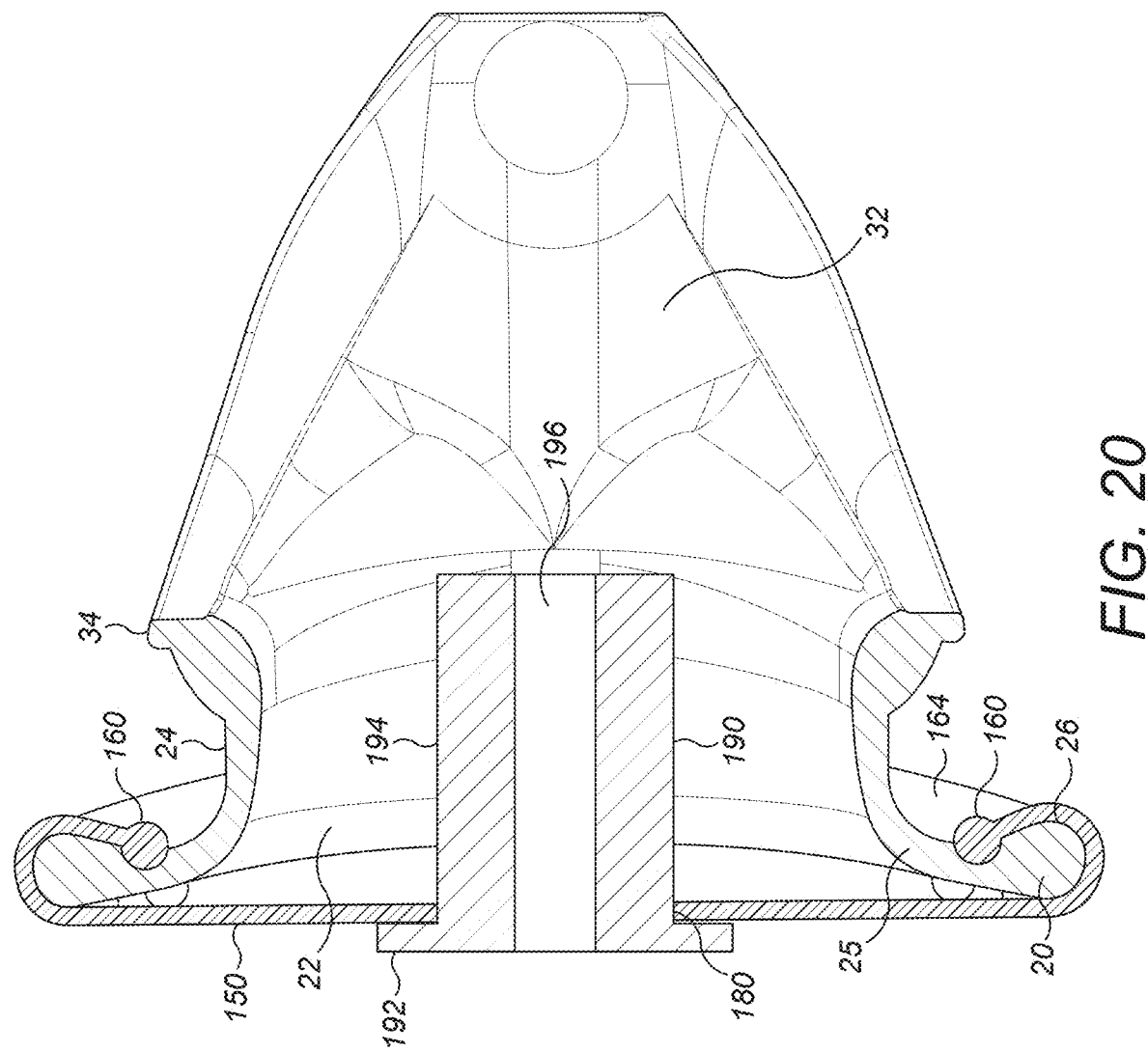
FIG. 20 is a cross-sectional side view of the dental retractor and sheet of FIG. 19 and further comprising a mouthpiece.

As best viewed in FIG. 20, the aperture 180 on the sheet 150 is configured to receive the mouthpiece 190 during an endoscopy procedure. The mouthpiece 190 is a hard plastics material which protects the endoscope from the patient's teeth. The mouthpiece 190 comprises a body portion 194 that is received within the aperture 180 and a flange 192 extending around an end of the body 194 and being configured to engage the sheet 150 such that the mouthpiece 190 is suspended from the sheet 150. The mouthpiece 190 is dimensioned such that the mouthpiece 190 may be received and located within the aperture 180. Furthermore, the body portion 194 may extend through the aperture 180, in use, such that the body portion 194 acts as a tongue retractor. The body portion 194 may engage the patient's tongue and retain it substantially flat against the floor of the patient's mouth thereby preventing the patient from moving their tongue and potentially contacting the endoscope during an endoscopy procedure.

The central aperture 180 comprises a reinforced section 182 or rim surrounding the aperture 180 so as to prevent the aperture 180 from tearing or deforming undesirably when it supports the endoscope. The rim 182 also provides support to the mouthpiece 190 thereby preventing the mouthpiece from moving axially during an endoscopy procedure. This is beneficial as the mouthpiece 190 is held steady during an endoscopy procedure thereby making the procedure easier for an operator to perform.

The dental retractor 10 beneficially controls the position of the patient's teeth, lips and cheeks when positioned within the patient's mouth. As such, the mouthpiece 190 and endoscope (not shown) may be placed within the patient's mouth without risking the patient's teeth damaging the endoscope or the endoscope damaging the patient's teeth. The dental retractor 10 and sheet 150 beneficially locate and retain the mouthpiece 190 in a stable position during a procedure thereby removing the requirement for a patient to bite on a mouthpiece to locate the endoscope.

As best viewed in FIG. 19, the sheet 150 comprises four apertures 158 for breathing and to allow access for a saliva ejector within the patient's mouth. The apertures 158 may be located at four corners of the sheet 150 to provide access to the left-hand and right-hand sides of the lower and upper dental arches.

Using the dental retractor 10 to control the position of the patient's teeth, cheeks and lips during an endoscopy procedure beneficially provides unobstructed access for an endoscope during an endoscopy procedure. Furthermore, the dental retractor 10 acts to stabilise the patient's mouth such that the endoscope may be retained within the mouthpiece 190 in a stable position within the patient's mouth.

It will be appreciated that various changes and modifications can be made to the present invention without departing from the scope of the present application.

The invention claimed is:

1. A dental retractor for controlling the position of soft tissue around and within a patient's mouth, the dental retractor comprising:
   a lip retractor for controlling the position of the patient's lips, wherein the lip retractor comprises a circumferentially continuous annular body and a circumferentially continuous radially extending flange extending radially from a proximal side of the annular body;
   a cheek retractor comprising a pair of arms for controlling the position of the patient's cheeks, wherein the pair of arms form an arch representative of a dental arch in plan view and extend distally from the annular body of the lip retractor;
   wherein the distally extending arms are configured to be located on an exterior of a dental arch of a patient and contact an upper and a lower labial sulcus and an upper and a lower buccal sulcus of the patient when the patient's mouth is both open and closed;
   a tongue retractor removably attachable to the cheek retractor for controlling the position of the patient's tongue, the tongue retractor including a strap for attaching the tongue retractor to the cheek retractor;
   wherein each arm of the cheek retractor comprises a channel arranged to receive the strap, and wherein the channel comprises an over-hanging lip to provide a snap-fit retention of the strap.

2. A dental retractor as claimed in claim 1, wherein the pair of arms taper as they extend distally.

3. A dental retractor as claimed in claim 1, wherein each arm comprises at least one deformable flange extending along an upper and/or lower edge of the arm.

4. A dental retractor as claimed in claim 3, wherein the flange increases in depth with distal progression along the arm.

5. A dental retractor as claimed in claim 1, wherein the lip retractor comprises at least one visual marker to indicate a centreline of the patient's mouth, in use.

6. A dental retractor as claimed in claim 1, wherein the lip retractor and/or the cheek retractor are substantially black on at least a surface positioned to face the patient's teeth.

7. A dental retractor as claimed in claim 1, wherein the strap is moveable along the channel to adjust the position of the tongue retractor relative to the cheek retractor.

8. A dental retractor as claimed in claim 1, wherein the strap comprises a tab for gripping the strap.

9. A dental retractor for controlling the position of soft tissue around and within a patient's mouth, the dental retractor comprising:

a lip retractor for controlling the position of the patient's lips;

a cheek retractor comprising a pair of arms for controlling the position of the patient's cheeks;

a tongue retractor removably attachable to the cheek retractor for controlling the position of the patient's tongue;

wherein the tongue retractor comprises a strap for attaching the tongue retractor to the cheek retractor;

wherein each arm of the cheek retractor comprises a channel arranged to receive the strap; and wherein the channel comprises an over-hanging lip to provide a snap-fit retention of the strap.

10. A dental retractor as claimed in claim 9, wherein the strap is moveable along the channel to adjust the position of the tongue retractor relative to the cheek retractor.

11. A dental retractor as claimed in claim 9, wherein the strap comprises a tab for gripping the strap.

* * * * *